(12) United States Patent
Gurram et al.

(10) Patent No.: US 7,157,581 B2
(45) Date of Patent: Jan. 2, 2007

(54) MONOCYCLIC COMPOUNDS AND THEIR USE IN MEDICINE: PROCESS FOR THEIR PREPARATION AND PHARMACEUTICAL COMPOSITIONS CONTAINING THEM

(75) Inventors: Ranga Madhavan Gurram, Hyderabad (IN); Venkateswarlu Akella, Hyderabad (IN); Rajagopalan Ramanujam, Hyderabad (IN); Ranjan Chakrabarti, Hyderabad (IN); Parimal Misra, Hyderabad (IN); Vidya Bhushan Lohray, Hyderabad (IN); Braj Bhushan Lohray, Hyderabad (IN); Rao Bheema Paraselli, Hyderabad (IN)

(73) Assignees: Dr. Reddy's Laboratories Ltd., Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 11/296,749

(22) Filed: Dec. 7, 2005

(65) Prior Publication Data

US 2006/0089500 A1  Apr. 27, 2006

Related U.S. Application Data

(60) Continuation of application No. 10/041,384, filed on Jan. 8, 2002, now Pat. No. 7,053,217, which is a division of application No. 09/507,371, filed on Feb. 18, 2000, now Pat. No. 6,369,067, which is a continuation-in-part of application No. 09/179,002, filed on Oct. 26, 1998.

(60) Provisional application No. 60/082,825, filed on Apr. 23, 1998.

(30) Foreign Application Priority Data

Oct. 27, 1997 (IN) ............... 2420/MAS/97

(51) Int. Cl.
    $C07D\ 239/02$    (2006.01)
(52) U.S. Cl. ..................................... 544/319
(58) Field of Classification Search .............. 544/319
    See application file for complete search history.

Primary Examiner—Bruck Kifle
(74) Attorney, Agent, or Firm—Milagros A. Cepeda; Edward D. Pergament; Robert A. Franks

(57) ABSTRACT

The present invention relates to novel antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), (I)

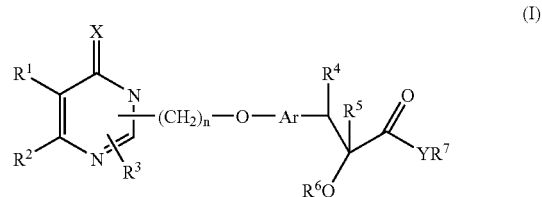

their derivatives, their analogs, their tautomeric forms, their stereoisomers, their polymorphs, their pharmaceutically acceptable salts, their pharmaceutically acceptable solvates and pharmaceutically acceptable compositions containing them. The present invention also relates to a process for the preparation of the above said novel compounds, their analogs, their derivatives, their tautomeric forms, their stereoisomers, their polymorphs, their pharmaceutically acceptable salts, pharmaceutically acceptable solvates and pharmaceutical compositions containing them. The present invention also relates to novel intermediates, processes for their preparation and their use in the preparation of compounds of formula (I).

2 Claims, No Drawings

MONOCYCLIC COMPOUNDS AND THEIR USE IN MEDICINE: PROCESS FOR THEIR PREPARATION AND PHARMACEUTICAL COMPOSITIONS CONTAINING THEM

CROSS-REFERENCE TO RELATED APPLICATIONS

This application is a continuation of copending U.S. patent application Ser. No. 10/041,384 filed Jan. 8, 2002 now U.S. Pat. No. 7,053,217, which is a divisional of U.S. patent application Ser. No. 09/507,371 filed Feb. 18, 2000, now U.S. Pat. No. 6,369,067, which is a continuation-in-part of U.S. patent application Ser. No. 09/179,002 filed Oct. 26, 1998, which claims the benefit of U.S. Provisional Patent Application No. 60/082,825 filed Apr. 23, 1998 and claims priority to Indian Application No. 2420/MAS/97 filed Oct. 27, 1997, the disclosure of which is incorporated herein by reference in its entirety.

FIELD OF THE INVENTION

The present invention relates to novel antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

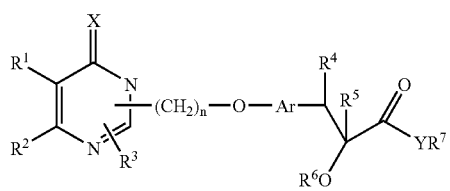

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates and pharmaceutical compositions containing them.

The present invention also relates to novel intermediates, processes for their preparation and their use in the preparation of compounds of formula (I).

The compounds of the present invention lower total cholesterol (TC); increase high density lipoprotein (HDL) and decrease low density lipoprotein (LDL), which have a beneficial effect on coronary heart disease and atherosclerosis.

The compounds of general formula (I) are useful in reducing body weight and for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The compounds of general formula (I) are also useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthorna, inflammation and for the treatment of cancer. The compounds of the present invention are useful in the treatment and/or prophylaxis of the above said diseases in combination/con-comittant with one or more HMG CoA reductase inhibitors, hypolipidemic/hypolipoproteinemic agents such as fibric acid derivatives, nicotinic acid, cholestyramine, colestipol, and probucol.

BACKGROUND OF THE INVENTION

Atherosclerosis and other peripheral vascular diseases are the major causes effecting the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations. (Stampfer et al., *N. Engl. J. Med.*, 325 (1991), 373–381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J.,* 282 (1981), 1741–1744) have shown that increase in HDL-particles may decrease the number of sites of stenosis in coronary arteries of human, and high level of HDL-cholesterol may protect against the progression of atherosclerosis. Picardo et al., (*Arteriosclerosis* 6 (1986) 434–441) have shown by in vitro experiment that HDL is capable of removing cholesterol from cells. They suggest that HDL may deplete tissues of excess free cholesterol and transfer it to liver (Macikinnon et al., *J. Biol. chem.* 261 (1986), 2548–2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of a large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyper-lipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause for cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ) isoform of PPAR (PPARγ) has been implicated in regulating differentiation of adipocytes (Endocrinology, (1994) 135: 798–800) and energy homeostasis (Cell, (1995) 83: 803–812), whereas the alpha (α) isoform of PPAR (PPARα) mediates fatty acid oxidation (Trend. Endocrin. Metab., (1993) 4: 291–296) thereby resulting in reduction of circulating free fatty acid in plasma (Current Biol. (1995) 5: 618–621). PPARα agonists have been found useful for the treatment of obesity (WO 97/36579). It has been recently disclosed that there exists synergism for the molecules, which are agonists for both PPARα and PPARγ and suggested to be useful for the treatment of syndrome X (WO 97/25042). Similar synergism between the insulin sensitizer (PPARγ agonist) and HMG CoA reductase inhibitor has been observed which may be useful for the treatment of atherosclerosis and xanthoma (EP 0 753 298).

It is known that PPARγ plays an important role in adipocyte differentiation (Cell, (1996) 87, 377–389). Ligand activation of PPAR is sufficient to cause complete terminal differentiation (Cell, (1994) 79, 1147–1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (Molecular Cell, (1998), 465–470; Carcinogenesis, (1998), 1949–53; Proc. Natl. Acad. Sci., (1997) 94, 237–241) and inhibition of expression of prostate cancer tissue (Cancer Research (1998) 58:3344–3352). This would be useful in the treatment of certain types of cancer, which express PPARγ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (Proc. Natl. Acad. Sci. (1996) 93, 5793–5796) have reported that insulin sensitizers which perhaps due to the PPAR agonist expression and therefore lower plasma leptin concentrations. However, it has been recently disclosed that compounds having insulin sensitizing property also possess leptin sensitization activity. They lower the circulating plasma leptin concentrations by improving the target cell response to leptin (WO/98/02159).

A few β-aryl-α-hydroxy propionic acids, their derivatives and their analogs have been reported to be useful in the treatment of hyperglycemia and hypercholesterolemia. Some of such compounds described in the prior art are outlined below:

i) U.S. Pat. No. 5,306,726, WO 91/19702 disclose several 3-aryl-2-hydroxypropionic acid derivatives of general formulas (IIa) and (IIb) as hypolipidemic and hypoglycemic agents.

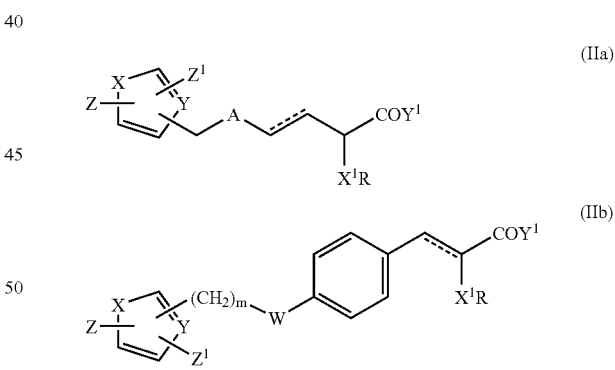

Examples of these compounds are shown in formulas (IIc) and (IId)

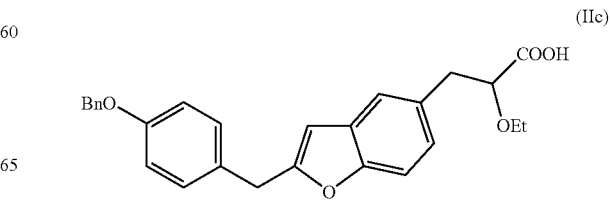

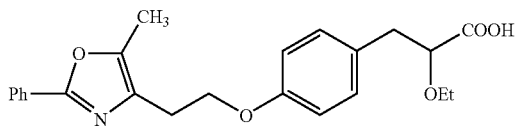

(IId)

ii) International Patent Applications, WO 95/03038 and WO 96/04260 disclose compounds of formula (IIe)

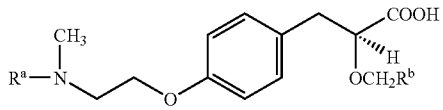

(IIe)

wherein $R^a$ represents 2-benzoxazolyl or 2-pyridyl and $R^b$ represent $CF_3$, $CH_2OCH_3$ or $CH_3$. A typical example is (S)-3-[4-[2-[N-(2-benzoxazolyl)-N-methylamino]ethoxy]phenyl]-2-(2,2-trifluoroethoxy)propanoic acid (IIf).

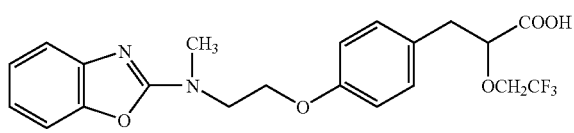

(IIf)

iii) International Patent Application Nos. WO 94/13650, WO 94/01420 and WO 95/17394 disclose the compounds of general formula (IIg)

$$A^1—X—(CH_2)_n—O—A^2—A^3—Y.R^2 \quad (IIg)$$

wherein $A^1$ represents aromatic heterocycle, $A^2$ represents substituted benzene ring and $A^3$ represents a moiety of formula $(CH_2)_m$—CH—$(OR^1)$, wherein $R^1$ represents alkyl groups, m is an integer; X represents substituted or unsubstituted N; Y represents C=O or C=S; $R^2$ represents $OR^3$ where $R^3$ may be alkyl, aralkyl, or aryl group; n represents an integer in the range of 2–6.

An example of these compounds is shown in formula (IIh)

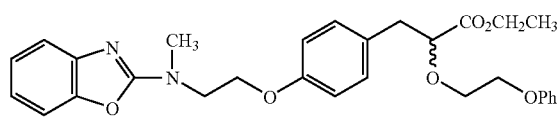

(IIh)

iv) International publication No. WO 99/08501 discloses compounds of general formula (IIi)

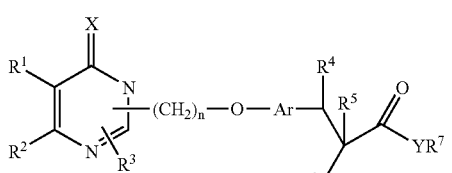

(IIi)

where X represents O or S; the groups $R^1$, $R^2$ and group $R^3$ when attached to the carbon atom, may be same or different and represent hydrogen, halogen, hydroxy, nitro, cyano, formyl or optionally substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, alkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^1$, $R^2$ along with the adjacent atoms to which they are attached may also form a 5–6 membered substituted or unsubstituted cyclic structure containing carbon atoms with one or more double bonds, which may optionally contain one or more heteroatoms selected from oxygen, nitrogen and sulfur; $R^3$ when attached to nitrogen atom represents hydrogen, hydroxy, formyl or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, alkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives, or sulfonic acid derivatives; the linking group represented by $—(CH_2)_n—O—$ may be attached either through nitrogen atom or through carbon atom where n is an integer ranging from 1–4; Ar represents an optionally substituted divalent single or fused aromatic or heterocyclic group; $R^4$ represents hydrogen atom, hydroxy, alkoxy, halogen, lower alkyl, optionally substituted aralkyl group or forms a bond together with the adjacent group $R^5$; $R^5$ represents hydrogen, hydroxy, alkoxy, halogen, lower alkyl group, acyl, optionally substituted aralkyl or $R^5$ forms a bond together with $R^4$; $R^6$ may be hydrogen, optionally substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, heteroaralkyl groups, with a provision that $R^6$ does not represent hydrogen when $R^7$ represents hydrogen or lower alkyl group; $R^7$ may be hydrogen or optionally substituted groups selected from alkyl, cycloalkyl, aryl, aralkyl, heterocyclyl, heteroaryl, heteroaralkyl groups; Y represents oxygen or $NR^8$, where $R^8$ represents hydrogen, alkyl, aryl, hydroxyalkyl, aralkyl, heterocyclyl, heteroaryl, heteroaralkyl groups; $R^7$ and $R^8$ together may form a substituted or unsubstituted 5 or 6 membered cyclic structure containing carbon atoms, which may optionally contain one or more heteroatoms selected from oxygen, sulfur or nitrogen.

An example of these compounds is shown in formula (IIj)

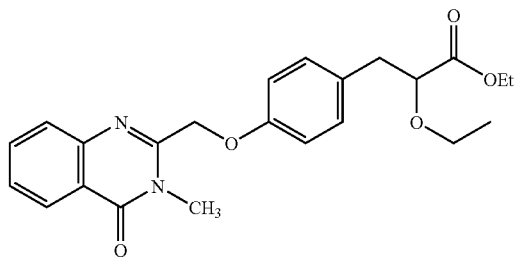

(IIj)

v) European publication No. EP 0903343 discloses compounds of general formula (IIk)

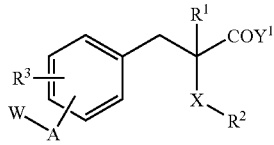
(IIk)

where A is an alkylene, alkyleneoxy or alkylenecarbonyl, X is O, S, NH or $CH_2$; $Y^1$ is an amino, hydroxylamino, hydroxyalkylamino, monoalkylamino, dialkylamino, cyclic amino, hydroxy or lower alkoxy group; $R^1$ is a hydrogen atom, lower alkyl, hydroxyalkyl group, alkoxyalkyl, halogenalkyl or $CoY^2$, where $Y^2$ is amino, hydroxyamino, hydroxyalkylamino, monoalkylamino, dialkylamino, cyclic amino, hydroxy or lower alkoxy group; $R^2$ is lower alkyl, hydroxyalkyl, alkoxyalkyl or halogenalkyl group, $COY^2$ or a phenyl, pyridyl or aralkyl which may be substituted and $R^3$ is a hydrogen or halogen, alkyl, alkoxy, halogenalkyl, amino, hydroxy or acyl groups or a salt thereof; W is a monocyclic or cyclic lactam ring selected from the following groups which may be substituted:

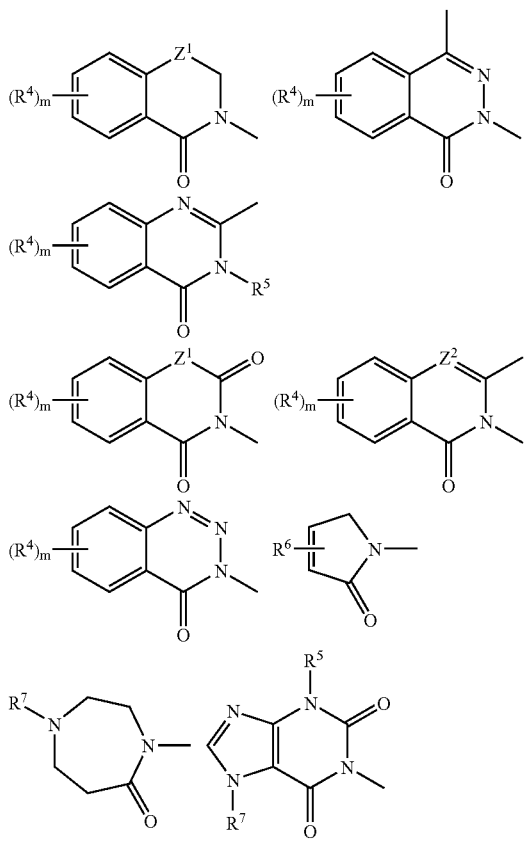

wherein $R^4$ is a hydrogen, halogen, alkyl, alkoxy, halogenalkyl, amino, hydroxy, cyano, carbonyl, acyl, nitro, carboxy or sulfonamide, phenyl or benzyl which may be substituted; $R^5$ is a hydrogen, alkyl, aryl, aralkyl or pyridyl which may be substituted; $R^6$ is hydrogen or lower alkyl group $R^7$ is a lower alkyl, phenyl or aralkyl groups; $Z^1$ is O, S, $CH_2$ or $NR^5$, $Z^2$ is N or CH and m is an integer of 1 to 4.

An example of these compounds is shown in formula (III)

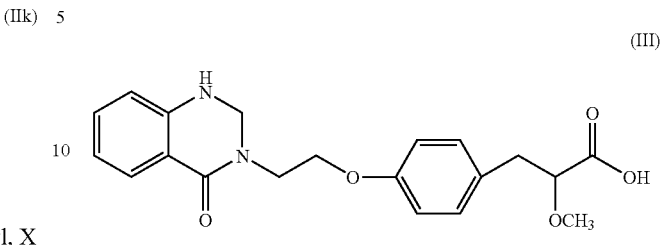
(III)

SUMMARY OF THE INVENTION

With an objective to develop novel compounds for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetes complications thereof, for the treatment of diseases wherein insulin resistance is the pathophysiological mechanism and for the treatment of hypertension, with better efficacy, potency and lower toxicity, we focussed our research to develop new compounds effective in the treatment of the above mentioned diseases. Effort in this direction has led to compounds having general formula (I).

The main objective of the present invention is therefore, to provide novel β-aryl-α-oxysubstituted alkylcarboxylic acids, their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel β-aryl-α-oxysubstituted alkylcarboxylic acids, their derivatives, their analogs, their tautomeric. forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Another objective of the present invention is to provide novel β-aryl-α-oxysubstituted alkylcarboxylic acids, their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another objective of the present invention is a process for the preparation of novel β-aryl-α-oxysubstituted alkylcarboxylic acids of formula (I), their derivatives, their analogs, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

Another objective of the present invention is to provide novel intermediates, a process for their preparation and their use in the preparation of β-aryl-α-oxysubstituted alkyl carboxylic acids of formula (I), their derivatives, their analogs, their tautomers, their stereoisomers, their polymorphs, their salts and their pharmaceutically acceptable solvates.

DETAILED DESCRIPTION OF THE INVENTION

β-aryl α-oxysubstituted propionic acids, their derivatives and their analogs of the present invention have the general formula (I)

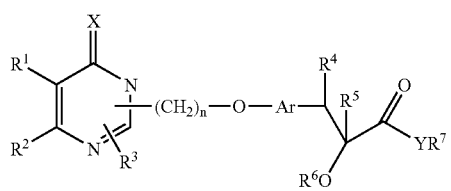

(I)

where X represents O or S; the groups $R^1$, $R^2$ and the group $R^3$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^3$ when attached to nitrogen atom represents hydrogen, hydroxy, formyl or substituted or unsubstituted groups selected from alkyl, cycloalkyl, alkoxy, cycloalkoxy, aryl, aralkyl, aryloxy, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives or sulfonic acid derivatives; the linking group represented by $-(CH_2)_n-O-$ may be attached either through nitrogen atom or through carbon atom where n is an integer ranging from 1–4; Ar represents a substituted or unsubstituted, divalent, single or fused, aromatic or heterocyclic group; $R^4$ represents hydrogen atom, halogen, hydroxy, lower alkyl, alkoxy, substituted or unsubstituted aralkyl group or forms a bond together with the adjacent group $R^5$; $R^5$ represents hydrogen, hydroxy, halogen, lower alkyl, alkoxy, acyl, substituted or unsubstituted aralkyl or $R^5$ forms a bond together with $R^4$; $R^6$ may be hydrogen atom or substituted or unsubstituted groups selected from alkyl, acyl, cycloalkyl, aryl, aralkyl, heterocyclyl, heteroaryl, heteroaralkyl, alkoxyalkyl, alkoxycarbonyl, aryloxycarbonyl, alkylaminocarbonyl, arylaminocarbonyl groups, with a provision that $R^6$ does not represent hydrogen when $R^7$ represents hydrogen or lower alkyl group; $R^7$ may be hydrogen or substituted or unsubstituted groups selected from alkyl, cycloalkyl, aryl, aralkyl, heterocyclyl, heteroaryl or heteroaralkyl groups; Y represents oxygen or $NR^8$, where $R^8$ represents hydrogen, or substituted or unsubstituted groups selected from alkyl, aryl, hydroxyalkyl, aralkyl, heterocyclyl, heteroaryl, heteroaralkyl groups; $R^7$ and $R^8$ together may form a substituted or unsubstituted 5 or 6 membered cyclic structure containing carbon atoms, a nitrogen atom and may optionally contain one or more additional heteroatoms selected from oxygen, sulfur or nitrogen.

Suitable groups represented by $R^1$, $R^2$ and the group $R^3$ when attached to carbon atom may be selected from hydrogen, halogen atom such as fluorine, chlorine, bromine, or iodine; hydroxy, cyano, nitro, formyl; substituted or unsubstituted $(C_1-C_{12})$alkyl group, especially, linear or branched $(C_1-C_{10})$alkyl group, such as methyl, ethyl, n-propyl, iso-propyl, n-butyl, iso-butyl, t-butyl, n-pentyl, iso-pentyl, hexyl, heptyl, octyl and the like; cyclo$(C_3-C_6)$alkyl group such as cyclopropyl, cyclobutyl, cyclopentyl, cyclohexyl and the like, the cycloalkyl group may be substituted; $(C_1-C_6)$alkoxy such as methoxy, ethoxy, propyloxy, butyloxy, iso-propyloxy and the like, the alkoxy group may be substituted; cyclo$(C_3-C_6)$alkoxy group such as cyclopropyloxy, cyclobutyloxy, cyclopentyloxy, cyclohexyloxy and the like, the cycloalkoxy group maybe substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, $C_6H_5CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heteroaralkyl group such as furanmethyl, pyridinemethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like which may be substituted; hydroxy$(C_1-C_6)$alkyl, which may be substituted; amino; acylamino groups such as $NHCOCH_3$, $NHCOC_2H_5$, $NHCOC_3H_7$, $NHCOC_6H_5$, and the like, which may be substituted; mono$(C_1-C_6)$alkylamino group such as $NHCH_3$, $NHC_2H_5$, $NHC_3H_7$, $NHC_6H_{13}$ and the like, which may be substituted; $(C_1-C_6)$dialkylamino group such as $N(CH_3)_2$, $NCH_3(C_2H_5)$ and the like, which may be substituted; arylamino group such as $HNC_6H_5$, $NCH_3(C_6H_5)$, $NHC_6H_4CH_3$, $NHC_6H_4$-Hal and the like, which may be substituted; aralkylamino group such as $C_6H_5CH_2NH$, $C_6H_5CH_2CH_2NH$, $C_6H_5CH_2NCH_3$ and the like, which may be substituted; amino$(C_1-C_6)$alkyl, which may be substituted; alkoxycarbonyl such as methoxycarbonyl, ethoxycarbonyl and the like, which may be substituted; aryloxycarbonyl group such as phenoxycarbonyl, naphthyloxycarbonyl and the like, which may be substituted; aralkoxycarbonyl group such as benzyloxycarbonyl, phenethyloxycarbonyl, naphthylmethoxycarbonyl and the like, which may be substituted; alkoxyalkyl group such as methoxymethyl, ethoxymethyl, methoxyethyl, ethoxyethyl and the like, the alkoxyalkyl groups may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; thio$(C_1-C_6)$alkyl, which may be substituted; $(C_1-C_6)$alkylthio, which may be substituted; alkoxycarbonylamino group such as $NHCOOC_2H_5$, $NHCOOCH_3$ and the like, which may be substituted; aryloxycarbonylamino group such as $NHCOOC_6H_5$, $NCH_3COOC_6H_5$, $NC_2H_5COOC_6H_5$, $NHCOOC_6H_4CH_3$, $NHCOOC_6H_4OCH_3$ and the like, which may be substituted; aralkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4OCH_3$ and the like, which may be substituted; carboxylic acid or its derivatives such as amides, like $CONH_2$, $CONHMe$, $CONMe_2$, $CONHEt$, $CONEt_2$, $CONHPh$ and the like, or esters such as $COOCH_3$, $COOC_2H_5$, $COOC_3H_7$ and the like, the carboxylic acid derivatives may be substituted; sulfonic acid or its derivatives such as amides like $SO_2NH_2$, $SO_2NHMe$, $SO_2NMe_2$, $SO_2NHCF_3$ and the like, or esters such as $SO_2CH_3$, $SO_2C_2H_5$, $SO_2C_3H_7$ and the like, the sulfonic acid derivatives may be substituted.

When the groups represented by $R^1$, $R^2$ and the group $R^3$ when attached to carbon atom are substituted, the substituents may be selected from halogen, hydroxy, nitro or substituted or unsubstituted groups selected from alkyl, cycloalkyl, alkoxy, cycloalkoxy, aryl, aralkyl, aryloxy, aralkoxy, aralkoxyalkyl, heterocyclyl, heteroaryl, heteroaralkyl, acyl, acyloxy, hydroxyalkyl, amino, acylamino, arylamino, aminoalkyl, alkoxycarbonyl, alkylamino, alkoxyalkyl, alkylthio, thioalkyl groups, carboxylic acid or its derivatives, or sulfonic acid or its derivatives.

It is preferred that the substituents on $R^1$ to $R^3$ represent halogen atom such as fluorine, chlorine, bromine, hydroxy group, optionally halogenated groups selected from alkyl group such as methyl, ethyl, isopropyl, n-propyl, n-butyl; cycloalkyl group such as cyclopropyl; aryl group such as phenyl; aralkyl group such as benzyl; $(C_1-C_3)$alkoxy, benzyloxy, acyl or acyloxy groups.

Suitable $R^3$ when attached to nitrogen atom is selected from hydrogen, hydroxy, formyl; substituted or unsubstituted $(C_1-C_{12})$alkyl group, especially, linear or branched $(C_1-C_6)$alkyl group, such as methyl, ethyl, n-propyl, iso-propyl, n-butyl, iso-butyl, t-butyl, n-pentyl, iso-pentyl, hexyl and the like; cyclo$(C_3-C_6)$alkyl group such as cyclopropyl, cyclobutyl, cyclopentyl, cyclohexyl and the like, the cycloalkyl group may be substituted; $(C_1-C_6)$alkoxy such as methoxy, ethoxy, propyloxy, butyloxy, iso-propyloxy and the like, the alkoxy group may be substituted; cyclo$(C_3-C_6)$ alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, $Hal-C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heteroaralkyl group such as furanmethyl, pyridinemethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like which may be substituted; hydroxy $(C_1-C_6)$alkyl, which may be substituted; amino; acylamino groups such as $NHCOCH_3$, $NHCOC_2H_5$, $NHCOC_3H_7$, $NHCOC_6H_5$, which may be substituted; mono$(C_1-C_6)$alkylamino group such as $NHCH_3$, $NHC_2H_5$, $NHC_3H_7$, $NHC_6H_{13}$ and the like, which may be substituted; $(C_1-C_6)$ dialkylamino group such as $N(CH_3)_2$, $NCH_3(C_2H_5)$ and the like, which may be substituted; arylamino group such as $HNC_6H_5$, $NCH_3(C_6H_5)$, $NHC_6H_4CH_3$, $NHC_6H_4$-Hal and the like, which may be substituted; aralkylamino group such as $C_6H_5CH_2NH$, $C_6H_5CH_2CH_2NH$, $C_6H_5CH_2NCH_3$ and the like, which may be substituted; amino$(C_1-C_6)$alkyl, which may be substituted; alkoxycarbonyl such as methoxycarbonyl, ethoxycarbonyl and the like, which may be substituted; aryloxycarbonyl group such as phenoxycarbonyl, naphthyloxycarbonyl and the like, which may be substituted; aralkoxycarbonyl group such as benzyloxycarbonyl, phenethyloxycarbonyl, naphthylmethoxycarbonyl and the like, which may be substituted; alkoxyalkyl group such as methoxymethyl, ethoxymethyl, methoxyethyl, ethoxyethyl and the like, the alkoxyalkyl groups may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; thio$(C_1-C_6)$alkyl, which may be substituted; $(C_1-C_6)$alkylthio, which may be substituted; carboxylic acid derivatives such as amides, like $CONH_2$, $CONHMe$, $CONMe_2$, $CONHEt$, $CONEt_2$, $CONHPh$ and the like or esters such as $COOCH_3$, $COOC_2H_5$, $COOC_3H_7$ and the like, the carboxylic acid derivatives may be substituted; sulfonic acid derivatives such as amides like $SO_2NH_2$, $SO_2NHMe$, $SO_2NMe_2$, $SO_2NHCF_3$ and the like or esters such as $SO_2CH_3$, $SO_2C_2H_5$, $SO_2C_3H_7$ and the like, the sulfonic acid derivatives may be substituted.

When the groups represented by $R^3$ attached to nitrogen are substituted, preferred substituents may be selected from halogen such as fluorine, chlorine; hydroxy, acyl, acyloxy, or amino groups.

n is an integer ranging from 1–4. It is preferred that n be 1 or 2.

Suitable groups represented by Ar include substituted or unsubstituted groups selected from divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl, benzoxazolyl and the like. The substituents on the group represented by Ar may be selected from substituted or unsubstituted linear or branched $(C_1-C_6)$alkyl, $(C_1-C_3)$alkoxy, halogen, acyl, amino, acylamino, thio or carboxylic or sulfonic acids and their derivatives.

It is preferred that Ar represents substituted or unsubstituted divalent phenylene, naphthylene, benzofuryl, indolyl, indolinyl, quinolinyl, azaindolyl, azaindolinyl, benzothiazolyl or benzoxazolyl.

It is more preferred that Ar is represented by divalent phenylene or naphthylene, which may be optionally substituted by methyl, halomethyl, methoxy or halomethoxy groups.

Suitable $R^4$ includes hydrogen, halogen atom such as fluorine, chlorine, bromine, or iodine; lower alkyl groups such as methyl, ethyl or propyl; hydroxy, $(C_1-C_3)$alkoxy such as methoxy, ethoxy, propoxy and the like; substituted or unsubstituted aralkyl such as benzyl, phenethyl and the like or $R^4$ together with $R^5$ represent a bond.

Suitable $R^5$ may be hydrogen, hydroxy, halogen atom such as fluorine, chlorine, bromine, or iodine; lower alkyl groups such as methyl, ethyl or propyl; $(C_1-C_3)$alkoxy such as methoxy, ethoxy, propoxy and the like; acyl group such as linear or branched $(C_2-C_{10})$acyl group such as acetyl, propanoyl, butanoyl, pentanoyl, benzoyl and the like; substituted or unsubstituted aralkyl such as benzyl, phenethyl and the like or together with $R^4$ forms a bond.

It is preferred that $R^4$ and $R^5$ represent hydrogen atom or $R^4$ and $R^5$ together represent a bond.

Suitable groups represented by $R^6$ may be selected from hydrogen, substituted or unsubstituted, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like; substituted or unsubstituted, linear or branched$(C_2–C_{16})$acyl group such as acetyl, propanoyl, butanoyl, benzoyl, octanoyl, decanoyl and the like; $(C_3–C_7)$cycloalkyl group such as cyclopropyl, cyclobutyl, cyclopentyl, cyclohexyl, and the like, the cycloalkyl group may be substituted; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; heterocyclyl group such as aziridinyl, pyrrolidinyl, piperidinyl and the like, the heterocyclyl group may be substituted; heteroaryl group such as pyridyl, thienyl, furyl and the like, the heteroaryl group may be substituted; heteroaralkyl group such as furanmethyl, pyridinemethyl, oxazolemethyl, oxazoleethyl and the like, the heteroaralkyl group may be substituted; $(C_1–C_6)$alkoxy$(C_1–C_6)$alkyl group such as methoxymethyl, ethoxymethyl, methoxyethyl, ethoxypropyl and the like, the alkoxyalkyl group may be substituted; $(C_1–C_6)$alkoxycarbonyl such as methoxycarbonyl, ethoxycarbonyl, propoxycarbonyl and the like, which may be substituted; aryloxycarbonyl such as phenoxycarbonyl, naphthyloxycarbonyl and the like, which may be substituted; $(C_1–C_6)$alkylaminocarbonyl, methylaminocarbonyl, ethylaminocarbonyl, propylaminocarbonyl and the like, which may be substituted; arylaminocarbonyl such as PhNHCO, naphthylaminocarbonyl and the like, which may be substituted. The substituents may be selected from halogen, hydroxy, or nitro or substituted or unsubstituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

Suitable groups represented by $R^7$ may be selected from hydrogen, substituted or unsubstituted, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like; $(C_3–C_7)$cycloalkyl such as cyclopropyl, cyclopentyl, cyclohexyl and the like, the cycloalkyl group may be substituted; aryl group such as phenyl, naphthyl and the like, the aryl group may be substituted; aralkyl group such as benzyl and phenethyl, the aralkyl group may be substituted; heterocyclyl group such as aziridinyl, pyrrolidinyl, piperidinyl and the like, the heterocyclyl group may be substituted; heteroaryl group such as pyridyl, thienyl, furyl and the like, the heteroaryl group may be substituted; heteroaralkyl group such as furanmethyl, pyridinemethyl, oxazolemethyl, oxazoleethyl and the like, the heteroaralkyl group may be substituted. The substituents on $R^7$ may be selected from the same group of $R^1$–$R^3$.

Suitable groups represented by $R^8$ may be selected from hydrogen, substituted or unsubstituted, linear or branched $(C_1–C_{16})$alkyl, preferably $(C_1–C_{12})$alkyl; aryl group such as phenyl, naphthyl and the like, the aryl group may be substituted; hydroxy$(C_1–C_6)$alkyl which may be substituted; aralkyl group such as benzyl and phenethyl and the like, the aralkyl group may be substituted; heterocyclyl group such as aziridinyl, pyrrolidinyl, piperidinyl, and the like, the heterocyclyl group may be substituted; heteroaryl group such as pyridyl, thienyl, furyl and the like the heteroaryl group may be substituted; heteroaralkyl group such as furanmethyl, pyridinemethyl, oxazolemethyl, oxazoleethyl and the like, the heteroaralkyl group may be substituted.

Suitable ring structures formed by $R^7$ and $R^8$ together may be selected from pyrrolidinyl, piperidinyl, morpholinyl, piperazinyl, oxazolinyl, diazolinyl and the like.

Suitable substituents on the cyclic structure formed by $R^7$ and $R^8$ taken together may be selected from halogen, hydroxy, alkyl, oxo, aralkyl and the like.

When any of the groups represented by $R^1$, $R^2$, $R^3$, $R^4$, $R^5$, $R^6$, $R^7$, Ar, $R^7$, $R^8$ or $R^7$ and $R^8$ taken together are substituted, the substituents are as defined above.

The compounds of formula (I) where $R^6$ represents hydrogen atom and $R^7$ represents hydrogen or lower alkyl groups have been described in our U.S. Pat. Nos. 5,885,997 and 5,985,884.

Pharmaceutically acceptable salts forming part of this invention include salts of the carboxylic acid moiety such as alkali metal salts like Li, Na, and K salts; alkaline earth metal salts like Ca and Mg salts; salts of organic bases such as diethanolamine, choline and the like; chiral bases like alkylphenylamine, phenyl glycinol and the like, salts of natural amino acids such as lysine, arginine, guanidine, methionine, alanine, valine, and the like; unnatural amino acids such as D-isomers or substituted amino acids; ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

(±) Ethyl 2-ethoxy-3-[4-[2-[2-ethyl-6-oxo-4-phenyl-1,6-dihydropyrimidin-1-yl]ethoxy]phenyl]propanoate;

(+) Ethyl 2-ethoxy-3-[4-[2-[2-ethyl-6-oxo-4-phenyl-1,6-dihydropyrimidin-1-yl]ethoxy]phenyl]propanoate;

(−) Ethyl 2-ethoxy-3-[4-[2-[2-ethyl-6-oxo-4-phenyl-1,6-dihydropyrimidin-1-yl]ethoxy]phenyl]propanoate;

(±) Ethyl 2-ethoxy-3-[4-[2-[2-methyl-6-oxo-4-phenyl-1,6-dihydropyrimidin-1-yl]ethoxy]phenyl]propanoate;

(+) Ethyl 2-ethoxy-3-[4-[2-[2-methyl-6-oxo-4-phenyl-1,6-dihydropyrimidin-1-yl]ethoxy]phenyl]propanoate;

(−) Ethyl 2-ethoxy-3-[4-[2-[2-methyl-6-oxo-4-phenyl-1,6-dihydropyrimidin-1-yl]ethoxy]phenyl]propanoate;

(±) Ethyl 2-ethoxy-3-[4-[2-[6-oxo-2-propyl-4-phenyl-1,6-dihydropyrimidin-1-yl]ethoxy]phenyl]propanoate;

(+) Ethyl 2-ethoxy-3-[4-[2-[6-oxo-2-propyl-4-phenyl-1,6-dihydropyrimidin-1-yl]ethoxy]phenyl]propanoate;

(−) Ethyl 2-ethoxy-3-[4-[2-[6-oxo-2-propyl-4-phenyl-1,6-dihydropyrimidin-1-yl]ethoxy]phenyl]propanoate;

(±) Ethyl 3-[4-[2-[2,5-diethyl-6-oxo-4-phenyl-1,6-dihydropyrimidin-1-yl]ethoxy]phenyl]-2-ethoxypropanoate;

(+) Ethyl 3-[4-[2-[2,5-diethyl-6-oxo-4-phenyl-1,6-dihydropyrimidin-1-yl]ethoxy]phenyl]-2-ethoxypropanoate;

(−) Ethyl 3-[4-[2-[2,5-diethyl-6-oxo-4-phenyl-1,6-dihydropyrimidin-1-yl]ethoxy]phenyl]-2-ethoxypropanoate;

(±) Ethyl 2-ethoxy-3-[4-[2-[2-isopropyl-6-oxo-4-phenyl-1,6-dihydropyrimidin-1-yl]ethoxy]phenyl]propanoate;

(+) Ethyl 2-ethoxy-3-[4-[2-[2-isopropyl-6-oxo-4-phenyl-1,6-dihydropyrimidin-1-yl]ethoxy]phenyl]propanoate;

(−) Ethyl 2-ethoxy-3-[4-[2-[2-isopropyl-6-oxo-4-phenyl-1,6-dihydropyrimidin-1-yl]ethoxy]phenyl]propanoate;

(±) Ethyl 2-ethoxy-3-[4-[2-[4-methyl-6-oxo-2-propyl-1,6-dihydropyrimidin-1-yl]ethoxy]phenyl]propanoate;

(+) Ethyl 2-ethoxy-3-[4-[2-[4-methyl-6-oxo-2-propyl-1,6-dihydropyrimidin-1-yl]ethoxy]phenyl]propanoate;

(−) Ethyl 2-ethoxy-3-[4-[2-[4-methyl-6-oxo-2-propyl-1,6-dihydropyrimidin-1-yl]ethoxy]phenyl]propanoate;

(±) Ethyl 3-[4-[2-[2,4-dimethyl-6-oxo-1,6-dihydropyrimidin-1-yl]ethoxy]phenyl]-2-ethoxypropanoate;

(+) Ethyl 3-[4-[2-[2,4-dimethyl-6-oxo-1,6-dihydropyrimidin-1-yl]ethoxy]phenyl]-2-ethoxypropanoate;
(−) Ethyl 3-[4-[2-[2,4-dimethyl-6-oxo-1,6-dihydropyrimidin-1-yl]ethoxy]phenyl]-2-ethoxypropanoate;
(±) Ethyl 2-ethoxy-3-[4-[2-[2-ethyl-6-oxo-4-trifluoromethyl-1,6-dihydropyrimidin-1-yl]ethoxy]phenyl]propanoate;
(+) Ethyl 2-ethoxy-3-[4-[2-[2-ethyl-6-oxo-4-trifluoromethyl-1,6-dihydropyrimidin-1-yl]ethoxy]phenyl]propanoate;
(−) Ethyl 2-ethoxy-3-[4-[2-[2-ethyl-6-oxo-4-trifluoromethyl-1,6-dihydropyrimidin-1-yl]ethoxy]phenyl]propanoate;
(±) Ethyl 2-ethoxy-3-[4-[2-[1-ethyl-6-oxo-4-phenyl-1,6-dihydropyrimidin-2-yl]ethoxy]phenyl]propanoate;
(+) Ethyl 2-ethoxy-3-[4-[2-[1-ethyl-6-oxo-4-phenyl-1,6-dihydropyrimidin-2-yl]ethoxy]phenyl]propanoate;
(−) Ethyl 2-ethoxy-3-[4-[2-[1-ethyl-6-oxo-4-phenyl-1,6-dihydropyrimidin-2-yl]ethoxy]phenyl]propanoate;
(±) Ethyl 2-ethoxy-3-[4-[2-[2-ethyl-4-(4-fluoro)phenyl-6-oxo-1,6-dihydropyrimidin-1-yl]ethoxy]phenyl]propanoate;
(+) Ethyl 2-ethoxy-3-[4-[2-[2-ethyl-4-(4-fluoro)phenyl-6-oxo-1,6-dihydropyrimidin-1-yl]ethoxy]phenyl]propanoate;
(−) Ethyl 2-ethoxy-3-[4-[2-[2-ethyl-4-(4-fluoro)phenyl-6-oxo-1,6-dihydropyrimidin-1-yl]ethoxy]phenyl]propanoate;
(±) Ethyl 2-ethoxy-3-[4-[2-[4-(4-chloro)phenyl-2-ethyl-6-oxo-1,6-dihydropyrimidin-1-yl]ethoxy]phenyl]propanoate;
(+) Ethyl 2-ethoxy-3-[4-[2-[4-(4-chloro)phenyl-2-ethyl-6-oxo-1,6-dihydropyrimidin-1-yl]ethoxy]phenyl]propanoate;
(−) Ethyl 2-ethoxy-3-[4-[2-[4-(4-chloro)phenyl-2-ethyl-6-oxo-1,6-dihydropyrimidin-1-yl]ethoxy]phenyl]propanoate;
(±) Ethyl 2-ethoxy-3-[4-[2-[2-ethyl-4-methyl-6-oxo-1,6-dihydropyrimidin-1-yl]ethoxy]phenyl]propanoate;
(+) Ethyl 2-ethoxy-3-[4-[2-[2-ethyl-4-methyl-6-oxo-1,6-dihydropyrimidin-1-yl]ethoxy]phenyl]propanoate;
(−) Ethyl 2-ethoxy-3-[4-[2-[2-ethyl-4-methyl-6-oxo-1,6-dihydropyrimidin-1-yl]ethoxy]phenyl]propanoate;
(±) 2-Ethoxy 3-[4-[2-[2-ethyl-6-oxo-4-phenyl-1,6-dihydropyrimidin-1-yl]ethoxy]phenyl]propanoic acid or its salts;
(+) 2-Ethoxy 3-[4-[2-[2-ethyl-6-oxo-4-phenyl-1,6-dihydropyrimidin-1-yl]ethoxy]phenyl]propanoic acid or its salts;
(−) 2-Ethoxy 3-[4-[2-[2-ethyl-6-oxo-4-phenyl-1,6-dihydropyrimidin-1-yl]ethoxy]phenyl]propanoic acid or its salts;
(±) 2-Ethoxy 3-[4-[2-[2-methyl-6-oxo-4-phenyl-1,6-dihydropyrimidin-1-yl]ethoxy]phenyl]propanoic acid or its salts;
(+) 2-Ethoxy 3-[4-[2-[2-methyl-6-oxo-4-phenyl-1,6-dihydropyrimidin-1-yl]ethoxy]phenyl]propanoic acid or its salts;
(−) 2-Ethoxy 3-[4-[2-[2-methyl-6-oxo-4-phenyl-1,6-dihydropyrimidin-1-yl]ethoxy]phenyl]propanoic acid or its salts;
(±) 2-Ethoxy 3-[4-[2-[6-oxo-2-propyl-4-phenyl-1,6-dihydropyrimidin-1-yl]ethoxy]phenyl]propanoic acid or its salts;
(+) 2-Ethoxy 3-[4-[2-[6-oxo-2-propyl-4-phenyl-1,6-dihydropyrimidin-1-yl]ethoxy]phenyl]propanoic acid or its salts;
(−) 2-Ethoxy 3-[4-[2-[6-oxo-2-propyl-4-phenyl-1,6-dihydropyrimidin-1-yl]ethoxy]phenyl]propanoic acid or its salts;
(±) 3-[4-[2-[2,5-Diethyl-6-oxo-4-phenyl-1,6-dihydropyrimidin-1-yl]ethoxy]phenyl]-2-ethoxypropanoic acid or its salts;
(+) 3-[4-[2-[2,5-Diethyl-6-oxo-4-phenyl-1,6-dihydropyrimidin-1-yl]ethoxy]phenyl]-2-ethoxypropanoic acid or its salts;
(−) 3-[4-[2-[2,5-Diethyl-6-oxo-4-phenyl-1,6-dihydropyrimidin-1-yl]ethoxy]phenyl]-2-ethoxypropanoic acid or its salts;
(±) 2-Ethoxy 3-[4-[2-[2-isopropyl-6-oxo-4-phenyl-1,6-dihydropyrimidin-1-yl]ethoxy]phenyl]propanoic acid or its salts;
(+) 2-Ethoxy 3-[4-[2-[2-isopropyl-6-oxo-4-phenyl-1,6-dihydropyrimidin-1-yl]ethoxy]phenyl]propanoic acid or its salts;
(−) 2-Ethoxy 3-[4-[2-[2-isopropyl-6-oxo-4-phenyl-1,6-dihydropyrimidin-1-yl]ethoxy]phenyl]propanoic acid or its salts;
(±) 2-Ethoxy 3-[4-[2-[4-methyl-6-oxo-2-propyl-1,6-dihydropyrimidin-1-yl]ethoxy]phenyl]propanoic acid or its salts;
(+) 2-Ethoxy 3-[4-[2-[4-methyl-6-oxo-2-propyl-1,6-dihydropyrimidin-1-yl]ethoxy]phenyl]propanoic acid or its salts;
(−) 2-Ethoxy 3-[4-[2-[4-methyl-6-oxo-2-propyl-1,6-dihydropyrimidin-1-yl]ethoxy]phenyl]propanoic acid or its salts;
(±) 3-[4-[2-[2,4-Dimethyl-6-oxo-1,6-dihydropyrimidin-1-yl]ethoxy]phenyl]-2-ethoxypropanoic acid or its salts;
(+) 3-[4-[2-[2,4-Dimethyl-6-oxo-1,6-dihydropyrimidin-1-yl]ethoxy]phenyl]-2-ethoxypropanoic acid or its salts;
(−) 3-[4-[2-[2,4-Dimethyl-6-oxo-1,6-dihydropyrimidin-1-yl]ethoxy]phenyl]-2-ethoxypropanoic acid or its salts;
(±) 2-Ethoxy 3-[4-[2-[2-ethyl-6-oxo-4-trifluoromethyl-1,6-dihydropyrimidin-1-yl]ethoxy]phenyl]propanoic acid or its salts;
(+) 2-Ethoxy 3-[4-[2-[2-ethyl-6-oxo-4-trifluoromethyl-1,6-dihydropyrimidin-1-yl]ethoxy]phenyl]propanoic acid or its salts;
(−) 2-Ethoxy 3-[4-[2-[2-ethyl-6-oxo-4-trifluoromethyl-1,6-dihydropyrimidin-1-yl]ethoxy]phenyl]propanoic acid or its salts;
(±) 2-Ethoxy 3-[4-[2-[1-ethyl-6-oxo-4-phenyl-1,6-dihydropyrimidin-2-yl]ethoxy]phenyl]propanoic acid or its salts;
(+) 2-Ethoxy 3-[4-[2-[1-ethyl-6-oxo-4-phenyl-1,6-dihydropyrimidin-2-yl]ethoxy]phenyl]propanoic acid or its salts;
(−) 2-Ethoxy 3-[4-[2-[1-ethyl-6-oxo-4-phenyl-1,6-dihydropyrimidin-2-yl]ethoxy]phenyl]propanoic acid or its salts;
(±) 2-Ethoxy 3-[4-[2-[2-ethyl-4-(4-fluoro)phenyl-6-oxo-1,6-dihydropyrimidin-1-yl]ethoxy]phenyl]propanoic acid or its salts;
(+) 2-Ethoxy 3-[4-[2-[2-ethyl-4-(4-fluoro)phenyl-6-oxo-1,6-dihydropyrimidin-1-yl]ethoxy]phenyl]propanoic acid or its salts;
(−) 2-Ethoxy 3-[4-[2-[2-ethyl-4-(4-fluoro)phenyl-6-oxo-1,6-dihydropyrimidin-1-yl]ethoxy]phenyl]propanoic acid or its salts;
(±) 2-Ethoxy 3-[4-[2-[4-(4-chloro)phenyl-2-ethyl-6-oxo-1,6-dihydropyrimidin-1-yl]ethoxy]phenyl]propanoic acid or its salts;
(+) 2-Ethoxy 3-[4-[2-[4-(4-chloro)phenyl-2-ethyl-6-oxo-1,6-dihydropyrimidin-1-yl]ethoxy]phenyl]propanoic acid or its salts;
(−) 2-Ethoxy 3-[4-[2-[4-(4-chloro)phenyl-2-ethyl-6-oxo-1,6-dihydropyrimidin-1-yl]ethoxy]phenyl]propanoic acid or its salts;
(±) 2-Ethoxy 3-[4-[2-[2-ethyl-4-methyl-6-oxo-1,6-dihydropyrimidin-1-yl]ethoxy]phenyl]propanoic acid or its salts;
(+) 2-Ethoxy 3-[4-[2-[2-ethyl-4-methyl-6-oxo-1,6-dihydropyrimidin-1-yl]ethoxy]phenyl]propanoic acid or its salts;
(−) 2-Ethoxy 3-[4-[2-[2-ethyl-4-methyl-6-oxo-1,6-dihydropyrimidin-1-yl]ethoxy]phenyl]propanoic acid or its salts;
[2R, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide and
[2S, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide;

According to a feature of the present invention, the compound of general formula (I) where $R^4$ and $R^5$ together represent a bond, Y represents oxygen atom, $R^1$, $R^2$, $R^3$, $R^6$, $R^7$, X, n and Ar are as defined earlier, can be prepared by any of the following routes shown in Scheme-I below.

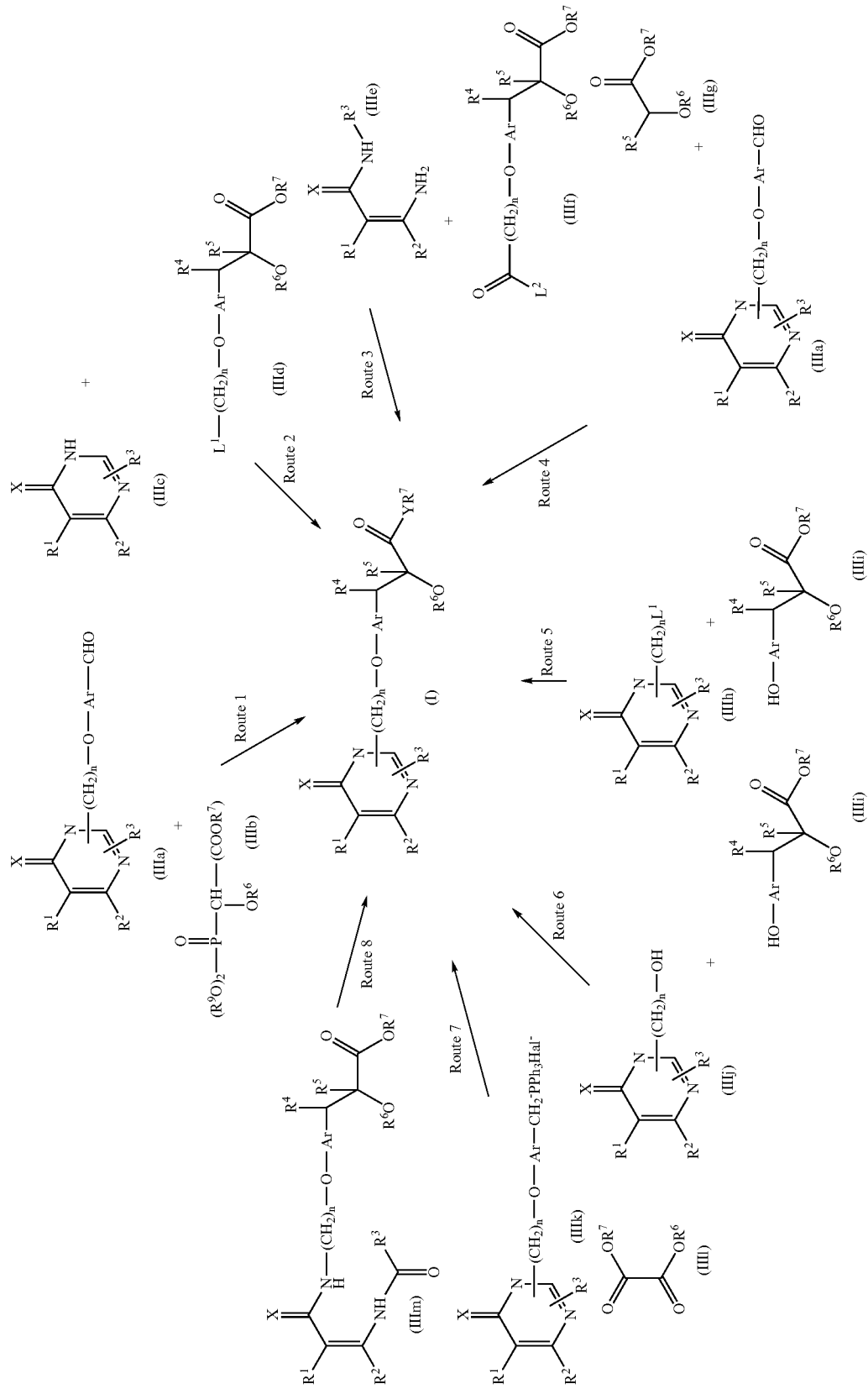

Route (1): The reaction of a compound of the general formula (IIIa) where all symbols are as defined earlier with a compound of formula (IIIb) where $R^9$ represents $(C_1-C_6)$ alkyl and all other symbols are as defined earlier to yield compound of general formula (I) where all symbols are as defined above may be carried out in the presence of a base such as alkali metal hydrides like NaH or KH; organolithiums such as $CH_3Li$, BuLi and the like; alkoxides such as NaOMe, NaOEt, $K^+BuO^-$ and the like or mixtures thereof. The reaction may be carried out in the presence of solvents such as THF, dioxane, DMF, DMSO, DME and the like or mixtures thereof. HMPA may be used as cosolvent. The reaction temperature may range from $-78°$ C. to $50°$ C., preferably at a temperature in the range of $-10°$ C. to $30°$ C. The reaction is more effective under anhydrous conditions. The compound of general formula (IIIb) may be prepared by Arbuzov reaction.

Alternatively, the compound of formula (I) may be prepared by reacting the compound of formula (IIIa) where all symbols are as defined earlier with Wittig reagents such as $Hal^-Ph_3P^+CH-(OR^6)CO_2R^7$ under similar reaction conditions as described above.

Route (2): The reaction of a compound of general formula (IIIc) where all symbols are as defined earlier with a compound of general formula (IIId) where $L^1$ is a leaving group such as halogen atom, p-toluenesulfonate, methanesulfonate, trifluoromethanesulfonate and the like, preferably a halogen atom; $R^4$, $R^5$ together represent a bond and all other symbols are as defined earlier to produce a compound of general formula (I) where $-(CH_2)_n-$ linker group is attached through the nitrogen atom and all other symbols are as defined above may be carried out in the presence of solvents such as DMSO, DMF, DME, THF, dioxane, ether and the like or mixtures thereof. The reaction may be carried out in an inert atmosphere which may be maintained by using inert gases such as $N_2$, Ar, He and the like. The reaction may be effected in the presence of a base such as alkalis like sodium hydroxide or potassium hydroxide; alkali metal carbonates such as sodium carbonate or potassium carbonate; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIc), preferably the amount of base ranges from 1 to 3 equivalents. Phase transfer catalysts such as tetraalkylammonium halide or hydroxide may be added. Additives such as alkali metal halides such as LiBr may be added: The reaction may be carried out at a temperature in the range of $0°$ C. to $150°$ C., preferably at a temperature in the range of $15°$ C. to $100°$ C. The duration of the reaction may range from 0.25 to 48 hours, preferably from 0.25 to 24 hours.

Route (3): The reaction of compound of general formula (IIIe) with a compound of general formula (IIIf) where $R^4$, $R^5$ together represent a bond, $L^2$ is halogen, $-OH$, $-OR^{10}$, $-O-C(=O)-OR^{10}$, where $R^{10}$ is $(C_1-C_5)$alkyl and all other symbols are as defined earlier to produce a compound of general formula (I) where $-(CH_2)_n-$ linker group is attached through the carbon atom and all other symbols are as defined above may be carried out in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar, He and the like. The reaction may be carried out at a temperature in the range of $50°$ C. to $200°$ C., preferably at a temperature in the range of $60°$ C. to $180°$ C. The reaction may be effected in the presence or in absence of a base or an acid. The nature of the base or the acid is not critical. Examples of such bases include organic bases such as pyridine, lutidine, triethyl amine, diisopropylethyl amine and the like; metal carbonates such as $K_2CO_3$ or $Na_2CO_3$. Examples of acids include organic acids such as AcOH, $C_2H_5COOH$, butyric acid, trifluoroacetic acid, p-toluenesulfonic acid, benzenesulfonic acid and the like; mineral acids such as HCl, HBr and the like. The duration of the reaction may range from 0.25 to 48 hours, preferably from 0.50 to 18 hours.

Route (4): The reaction of a compound of the general formula (IIIa) where all symbols are as defined earlier, with a compound of formula (IIIg) where $R^5$ represents hydrogen atom and all other symbols are as defined earlier may be carried out in the presence of a base. The nature of the base is not critical. Any base normally employed for aldol condensation reaction may be employed; bases like metal hydride such as NaH, KH, metal alkoxides such as NaOMe, $t-BuO^-K^+$, NaOEt, metal amides such as $LiNH_2$, $LiN(ipr)_2$ may be used. Aprotic solvents such as THF, ether, dioxane may be used. The reaction may be carried out in an inert atmosphere which may be maintained by using inert gases such as $N_2$, Ar, or He and the reaction is more effective under anhydrous conditions. Temperature in the range of $-80°$ C. to $35°$ C. may be used. The β-hydroxy product initially produced may be dehydrated under conventional dehydration conditions such as treating with pTSA in solvents such as benzene or toluene. The nature of solvent and dehydrating agent is not critical. Temperature in the range of $20°$ C. to reflux temperature of the solvent used may be employed, preferably at reflux temperature of the solvent by continuous removal of water using a Dean Stark water separator.

Route (5): The reaction of compound of formula (IIIh) where all symbols are as defined earlier and $L^1$ represents a leaving group such as halogen atom, p-toluenesulfonate, methanesulfonate, trifluoromethanesulfonate and the like, preferably a halogen atom with compound of formula (IIIi) where $R^4$ and $R^5$ together represent a bond and all other symbols are as defined earlier to produce a compound of the formula (I) defined above may be carried out in the presence of aprotic solvents such as THF, DMF, DMSO, DME and the like or mixtures thereof. The reaction may be carried out in an inert atmosphere which may be maintained by using inert gases such as $N_2$, Ar, He and the like. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from $0°$ C.–$120°$ C., preferably at a temperature in the range of $30°$ C.–$100°$ C. The duration of the reaction may range from 1 to 24 hours, preferably from 2 to 12 hours. The compound of formula (IIIi) can be prepared according to known procedure by a Wittig Horner reaction between the hydroxy protected aryl aldehyde such as benzyloxyaryl aldehyde and the compound of formula (IIIb), followed by deprotection.

Route (6): The reaction of compound of general formula (IIIj) where all symbols are as defined earlier with a compound of general formula (IIIi) where $R^4$ and $R^5$ together represent a bond and all other symbols are as defined earlier may be carried out using suitable coupling agents such as dicyclohexyl urea, triarylphosphine/dialkylazadicarboxylate such as $PPh_3/DEAD$ and the like. The reaction may be carried out in the presence of solvents such as THF, DME, $CH_2Cl_2$, $CHCl_3$, toluene, acetonitrile, carbon tetrachloride and the like. The inert atmosphere may be maintained by using inert gases such as $N_2$, Ar and the like. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route (7): The reaction of a compound of formula (IIIk) where all symbols are as defined earlier with a compound of formula (IIII) where $R^6=R^7$ and are as defined earlier excluding hydrogen, to produce a compound of the formula (I) where $R^4$ and $R^5$ together represent a bond may be carried out neat in the presence of a base such as alkali metal hydrides like NaH, KH or organolithiums like $CH_3Li$, BuLi and the like or alkoxides such as NaOMe, NaOEt, t-BuO$^-$K$^+$ and the like or mixtures thereof. The reaction may be carried out in the presence of aprotic solvents such as THF, dioxane, DMF, DMSO, DME and the like or mixtures thereof. HMPA may be used as cosolvent. The reaction temperature may range from $-78°$ C. to 100° C., preferably at a temperature in the range of $-10°$ C. to 50° C.

Route (8): The cyclisation of a compound of general formula (IIIm), where $R^4$ and $R^5$ together represent a bond, $R^7$ is as defined earlier excluding hydrogen and all symbols are as defined earlier to produce a compound of general formula (I), where —$(CH_2)_n$— linker group is attached through nitrogen atom and all other symbols are as defined earlier may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar, He and the like. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Examples of such bases include organic bases such as pyridine, lutidine, triethyl amine, diisopropylethyl amine and the like, metal carbonates such as $K_2CO_3$, $Na_2CO_3$. Examples of acids include organic acids such as AcOH, $C_2H_5COOH$, butyric acid, trifluoroacetic acid, p-toluenesulfonic acid, benzenesulfonic acid and the like, mineral acids such as HCl, HBr and the like. The duration of the reaction may range from 0.25 to 48 hours, preferably from 0.50 to 18 hours.

In yet another embodiment of the present invention, the compound of the general formula (I) where $R^4$ represents hydrogen atom, hydroxy, alkoxy, halogen, lower alkyl, substituted or unsubstituted aralkyl group; $R^5$ represents hydrogen, hydroxy, alkoxy, halogen, lower alkyl group, acyl or substituted or unsubstituted aralkyl; $R^1$, $R^2$, $R^3$, $R^6$, $R^7$, X, n and Ar are as defined earlier and Y represents oxygen atom can be prepared by one or more of the processes shown in Scheme-II below.

Scheme-II

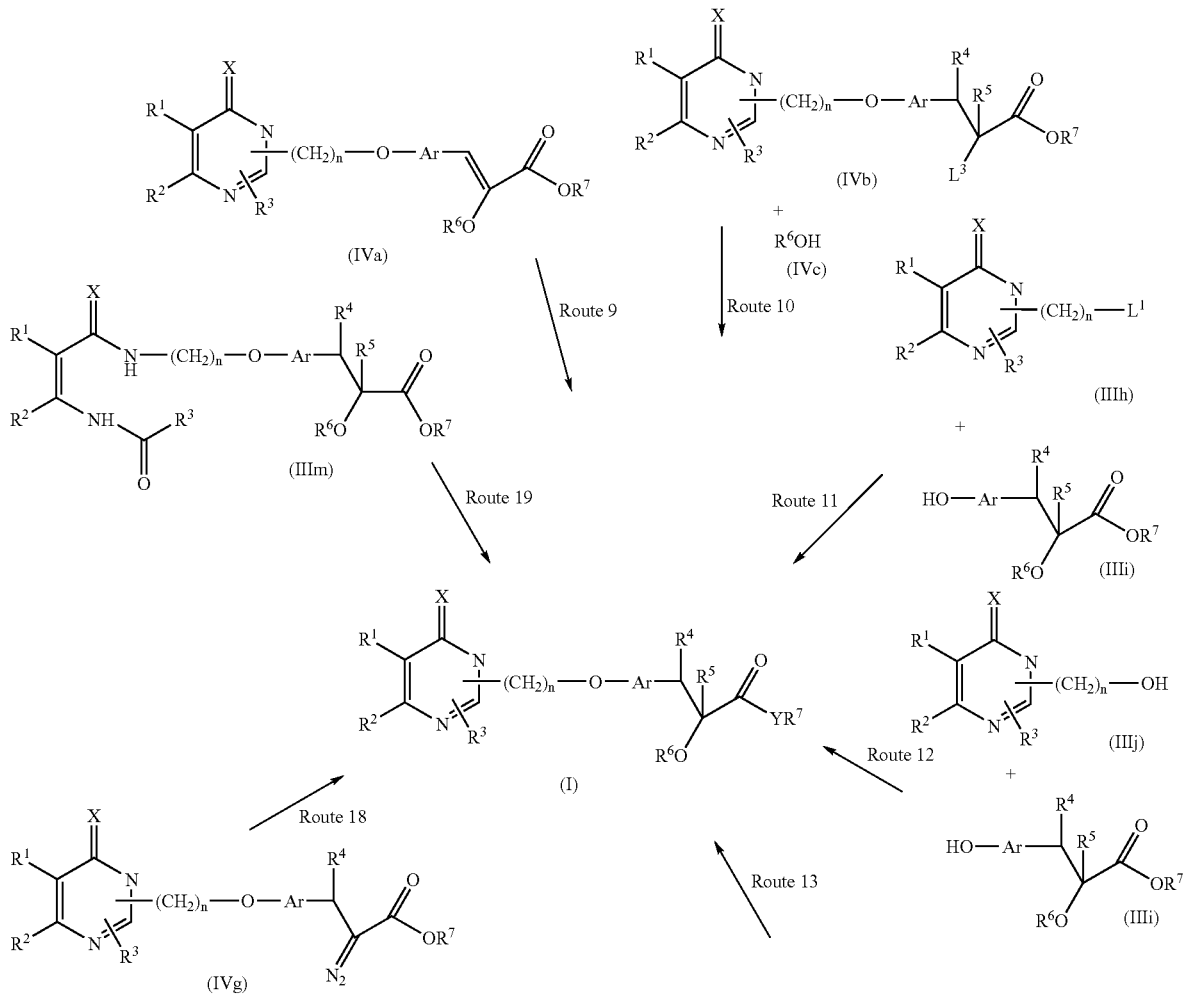

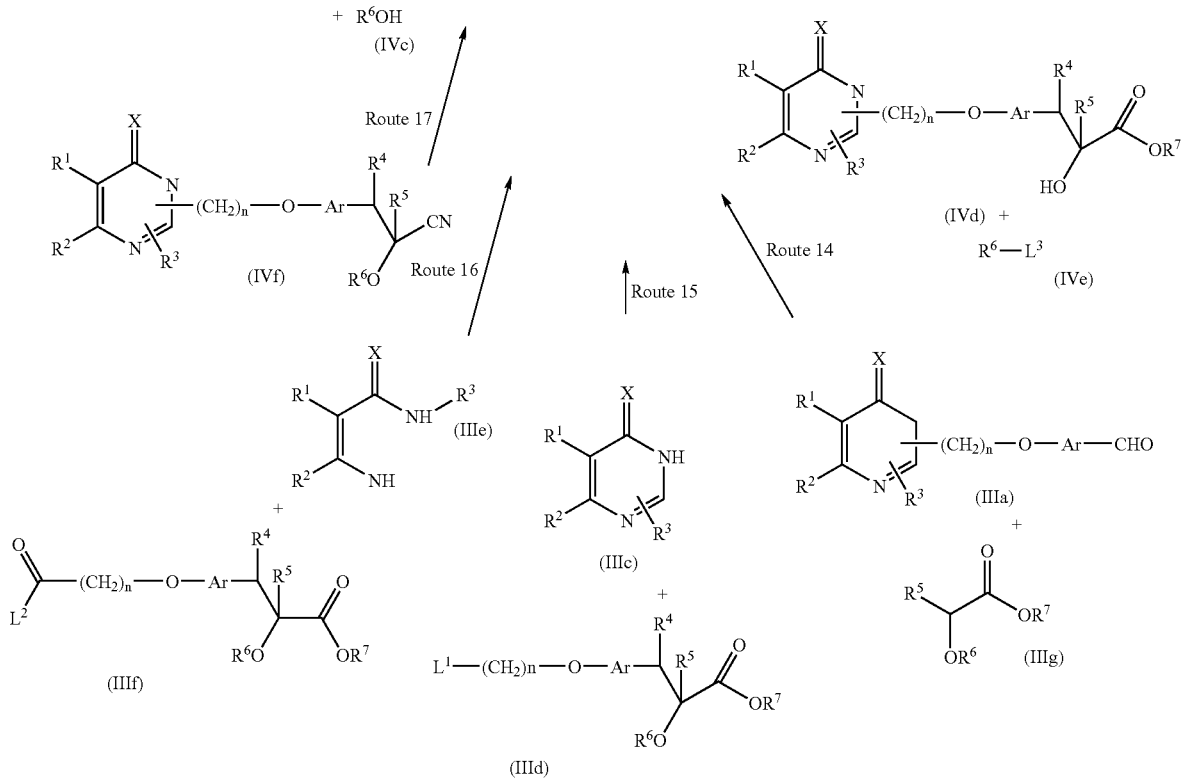

Route (9): The reduction of compound of the formula (IVa) which represents a compound of formula (I) where $R^4$ and $R^5$ together represent a bond and Y represent oxygen atom and all other symbols are as defined earlier, obtained as described earlier (Scheme-I), to yield a compound of the general formula (I) where $R^4$ and $R^5$ each represent hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate, alcohol such as methanol, ethanol and the like. A pressure between atmospheric pressure and 80 psi may be employed. The catalyst may be preferably 5–10% Pd/C and the amount of catalyst used may range from 5–100% w/w. The reaction may also be carried out by employing metal solvent reduction such as magnesium in alcohol or sodium amalgam in alcohol, preferably methanol. The hydrogenation may be carried out in the presence of metal catalysts containing chiral ligands to obtain a compound of formula (I) in optically active form. The metal catalyst may contain Rhodium, Ruthenium, Indium and the like. The chiral ligands may preferably be chiral phosphines such as optically pure enantiomers of 2,3-bis(diphenylphosphino)butane, 1,2-bis(diphenylphosphino)ethane, 1,2-bis(2-methoxyphenyl phenylphosphino)ethane, 2,3-isopropylidene-2,3-dihydroxy-1,4-bis(diphenylphosphino)butane and the like. Any suitable chiral catalyst may be employed which would give required optical purity of the product (I) (Ref: Principles of Asymmetric Synthesis, Tetrahedron Series Vol 14, pp 311–316, Ed. Baldwin J. E.).

Route (10): The reaction of compound of formula (IVb) where $R^7$ is as defined earlier excluding hydrogen all other symbols are as defined earlier and $L^3$ is a leaving group such as halogen atom with an alcohol of general formula (IVc), where $R^6$ is as defined earlier excluding hydrogen to produce a compound of the formula (I) defined earlier may be carried out in the presence of solvents such as THF, DMF, DMSO, DME and the like or mixtures thereof. The reaction may be carried out in an inert atmosphere which may be maintained by using inert gases such as $N_2$, Ar, He and the like. The reaction may be effected in the presence of a base such as KOH, NaOH, NaOMe, NaOEt, t-BuO⁻K⁺ or NaH or mixtures thereof. Phase transfer catalysts such as tetraalkylammonium halides or hydroxides may be employed. The reaction temperature may range from 20° C.–120° C., preferably at a temperature in the range of 30° C.–100° C. The duration of the reaction may range from 1 to 12 hours, preferably from 2 to 6 hours. The compound of general formula (IVb) where $R^7$ represents hydrogen or lower alkyl group and its preparation has been disclosed in our U.S. Pat. Nos. 5,885,997 and 5,985,884.

Route (11): The reaction of compound of formula (IIIh) defined earlier with compound of formula (IIIi) where all symbols are as defined earlier to produce a compound of the formula (I) defined above, may be carried out in the presence of solvents such as THF, DMF, DMSO, DME and the like or mixtures thereof. The reaction may be carried out in an inert atmosphere which is maintained by using inert gases such as $N_2$, Ar, He and the like. The reaction may be effected in the presence of a base such as $K_2CO_3$, $Na_2CO_3$, NaH and the like or mixtures thereof. Acetone may be used as a solvent when $K_2CO_3$ or $Na_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours. The compound of formula (IIIi) may be prepared by Wittig Horner reaction between the protected hydroxyaryl aldehyde and compound of formula (IIIj) followed by reduction of the double bond and deprotection. Alternatively, the compound of formula (IIIi) may be prepared by following a procedure disclosed in WO 94/01420.

Route 12: The reaction of compound of general formula (IIIj) defined earlier with a compound of general formula (IIIi) where all symbols are as defined above may be carried out using suitable coupling agents such as dicyclohexyl urea, driarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbon tetrachloride and the like. The inert atmosphere may be maintained by using inert gases such as $N_2$, Ar, He and the like. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route 13: The reaction of compound of formula (IVd) which represents a compound of formula (I) where $R^6$ represents hydrogen atom and all other symbols are as defined above with a compound of formula (IVe) and is as defined earlier excluding hydrogen and $L^3$ is a halogen atom may be carried out in the presence of solvents such as THF, DMF, DMSO, DME and the like. The inert atmosphere may be maintained by using inert gases such as $N_2$, Ar, He and the like. The reaction may be effected in the presence of a base such as KOH, NaOH, NaOMe, t-BuO$^-$K$^+$, NaH and the like. Phase transfer catalyst such as tetraalkylammonium halides or hydroxides may be employed. The reaction temperature may range from 20° C. to 150° C., preferably at a temperature in the range of 30° C. to 100° C. The duration of the reaction may range from 1 to 24 hours, preferably from 2 to 6 hours.

The compound of formula (IVd) where $R^7$ represents hydrogen or lower alkyl group and its preparation has been described in our U.S. Pat. Nos. 5,885,997 and 5,985,884. The compound of formula (IVd) represents a compound of formula (I) where $R^6$ represents hydrogen atom and all other symbols are as defined earlier.

Route (14): The reaction of a compound of the general formula (IIIa) as defined above with a compound of formula (IIIg) where $R^5$ represents hydrogen atom and all other symbols are as defined earlier may be carried out under conventional conditions. The base is not critical. Any base normally employed for aldol condensation reaction may be employed, metal hydride such as NaH or KH; metal alkoxides such as NaOMe, t-BuO$^-$K$^t$ or NaOEt; metal amides such as $LiNH_2$, $LiN(iPr)_2$. Aprotic solvent such as THF may be used. Inert atmosphere may be employed such as argon and the reaction is more effective under anhydrous conditions. Temperature in the range of −80° C. to 25° C. may be used. The β-hydroxy aldol product may be dehydroxylated using conventional methods, conveniently by ionic hydrogenation technique such as by treating with a trialkyl silane in the presence of an acid such as trifluoroacetic acid. Solvent such as $CH_2Cl_2$ may be used. Favorably, reaction proceeds at 25° C. Higher temperature may be employed if the reaction is slow.

Route (15): The reaction of a compound of general formula (IIIc) where all symbols are as defined earlier with a compound of general formula (IIId) where $L^1$ is a leaving group such as halogen atom, p-toluenesulfonate, methanesulfonate, trifluoro-methanesulfonate and the like, preferably a halogen atom and all other symbols are as defined earlier to produce a compound of general formula (I) where —$(CH_2)_n$— is attached through nitrogen atom and all other symbols are as defined above may be carried out in the presence of solvents such as DMSO, DMF, DME, THF, dioxane, ether and the like or a combination thereof. The reaction may be carried out in an inert atmosphere which may be maintained by using inert gases such as $N_2$, Ar, He and the like. The reaction may be effected in the presence of a base such as alkalis like sodium hydroxide, potassium hydroxide; alkali metal carbonates like sodium carbonate or potassium carbonate; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIc), preferably the amount of base ranges from 1 to 3 equivalents. Additives such as alkali metal halides such as LiBr may be added. The reaction may be carried out at a temperature in the range of 0° C. to 150° C., preferably at a temperature in the range of 15° C. to 100° C. The duration of the reaction may range from 0.25 to 48 hours, preferably from 0.25 to 24 hours.

Route (16): The reaction of compound of general formula (IIIe) as defined earlier with a compound of general formula (IIIf) where $L^2$ is halogen, —OH, —OR$^{10}$, —O—C(=O)—OR$^{10}$, where $R^{10}$ is ($C_1$–$C_5$)alkyl and all other symbols are as defined earlier, to produce a compound of general formula (I) where —$(CH_2)_n$— is attached through carbon atom and all other symbols are as defined above may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar, He and the like. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Examples of such bases include organic bases such as pyridine, lutidine, triethyl amine, diisopropylethyl amine and the like, metal carbonates such as $K_2CO_3$ or $Na_2CO_3$. Examples of acids include organic acids such as AcOH, $C_2H_5COOH$, butyric acid, trifluoroacetic acid, p-toluenesulfonic acid, benzenesulfonic acid and the like, mineral acids such as HCl, HBr and the like. The duration of the reaction may range from 0.25 to 48 hours, preferably from 0.50 to 18 hours.

Route (17): The conversion of compound of formula (IVf) where all symbols are as defined earlier to a compound of formula (I) may be carried out either in the presence of base or acid and the selection of base or acid is not critical. Any base normally used for hydrolysis of nitrile to acid may be employed, metal hydroxides such as NaOH or KOH in an aqueous solvent or any acid normally used for hydrolysis of nitrile to ester may be employed such as dry HCl in an excess of alcohol such as methanol, ethanol, propanol etc. The reaction may be carried out at a temperature in the range of 0° C. to reflux temperature of the solvent used, preferably at a temperature in the range of 25° C. to reflux temperature of the solvent used. The duration of the reaction may range from 0.25 to 48 hrs.

Route (18): The reaction of a compound of formula (IVg) where $R^7$ is as defined earlier excluding hydrogen and all symbols are as defined earlier with a compound of formula (IVc) where $R^6$ is as defined earlier excluding hydrogen to produce a compound of formula (I) (by a rhodium carbenoid mediated insertion reaction) may be carried out in the presence of rhodium (II) salts such as rhodium (II) acetate. The reaction may be carried out in the presence of solvents such as benzene, toluene, dioxane, ether, THF and the like or a combination thereof or when practicable in the presence of $R^6$OH as solvent at any temperature providing a convenient rate of formation of the required product, generally at an elevated temperature, such as reflux temperature of the solvent. The inert atmosphere may be maintained by using inert gases such as $N_2$, Ar, He and the like. The duration of the reaction may range from 0.5 to 24 h, preferably from 0.5 to 6 h.

Route (19): The cyclisation of compound of general formula (IIIm), where $R^7$ is as defined earlier excluding hydrogen and all other symbols are as defined above and all other symbols are as defined earlier to produce a compound of general formula (I), where —$(CH_2)_n$— linker group is attached through nitrogen atom and all other symbols are as defined earlier may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar, He and the like. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Examples of such bases include organic bases such as pyridine, lutidine, triethyl amine, diisopropylethyl amine and the like, metal carbonates such as $K_2CO_3$ or $Na_2CO_3$. Examples of acids include organic acids such as AcOH, $C_2H_5COOH$, butyric acid, trifluoroacetic acid, p-toluenesulfonic acid, benzenesulfonic acid and the like, mineral acids such as HCl, HBr and the like. The duration of the reaction may range from 0.25 to 48 hours, preferably from 0.50 to 18 hours.

The compound of general formula (I) where $R^7$ represents hydrogen atom may be prepared by hydrolysing using conventional methods, a compound of formula (I) where $R^7$ represents all groups defined earlier except hydrogen. The hydrolysis may be carried out in the presence of a base such as $Na_2CO_3$ and a suitable solvent such as methanol, ethanol and the like or mixtures thereof. The reaction may be carried out at a temperature in the range of 20–120° C., preferably at 25–30° C. The reaction time may range from 2 to 48 h, preferably from 4 to 12 h.

The compound of general formula (I) where Y represents oxygen and $R^7$ is as defined earlier may be converted to compound of formula (I), where Y represents $NR^8$ by reaction with appropriate amines. Suitably the compound of formula (I) where $YR^7$ represents OH may be converted to acid halide, preferably $YR^7$=halogen, by reacting with appropriate reagents such as oxalyl chloride, thionyl chloride and the like, followed by treatment with amines; Alternatively, mixed anhydrides may be prepared from compound of formula (I) where $YR^7$ represents OH and all other symbols are as defined earlier by treating with acid halides such acetyl chloride, acetyl bromide, pivaloyl chloride, dichlorobenzoyl chloride and the like. The reaction may be carried out in the presence of suitable base such as pyridine, triethylamine, diisopropyl ethylamine and the like. Solvents such as halogenated hydrocarbons like $CHCl_3$, $CH_2Cl_2$, hydrocarbons such as benzene, toluene, xylene and the like may be used. The reaction may be carried out at a temperature in the range of –40° C. to 40° C., preferably 0° C. to 20° C. The acid halide or mixed anhydride thus prepared may further be treated with appropriate amines.

In another embodiment of the present invention there is provided the novel intermediates of formula (IVf)

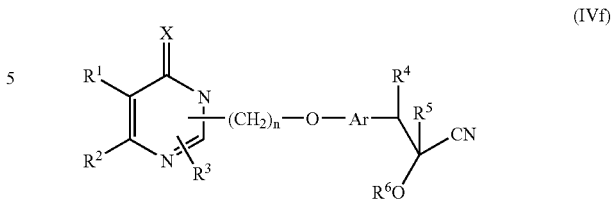

(IVf)

where X represents O or S; the groups $R^1$, $R^2$ and the group $R^3$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^3$ when attached to nitrogen atom represents hydrogen, hydroxy, formyl or substituted or unsubstituted groups selected from alkyl, cycloalkyl, alkoxy, cycloalkoxy, aryl, aralkyl, aryloxy, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives or sulfonic acid derivatives; the linking group represented by $-(CH_2)_n-O-$ may be attached either through nitrogen atom or through carbon atom where n is an integer ranging from 1–4; Ar represents a substituted or unsubstituted, divalent, single or fused, aromatic or heterocyclic group; $R^4$ represents hydrogen atom, halogen, hydroxy, lower alkyl, alkoxy, substituted or unsubstituted aralkyl group or forms a bond together with the adjacent group $R^5$; $R^5$ represents hydrogen, hydroxy, halogen, lower alkyl, alkoxy, acyl, substituted or unsubstituted aralkyl or $R^5$ forms a bond together with $R^4$; $R^6$ may be hydrogen atom or substituted or unsubstituted groups selected from alkyl, acyl, cycloalkyl, aryl, aralkyl, heterocyclyl, heteroaryl, heteroaralkyl, alkoxyalkyl, alkoxycarbonyl, aryloxycarbonyl, alkylaminocarbonyl, arylaminocarbonyl groups, and a process for its preparation and its use in the preparation of β-aryl-α-oxysubstituted alkylcarboxylic acids is provided (Scheme-III).

Scheme III

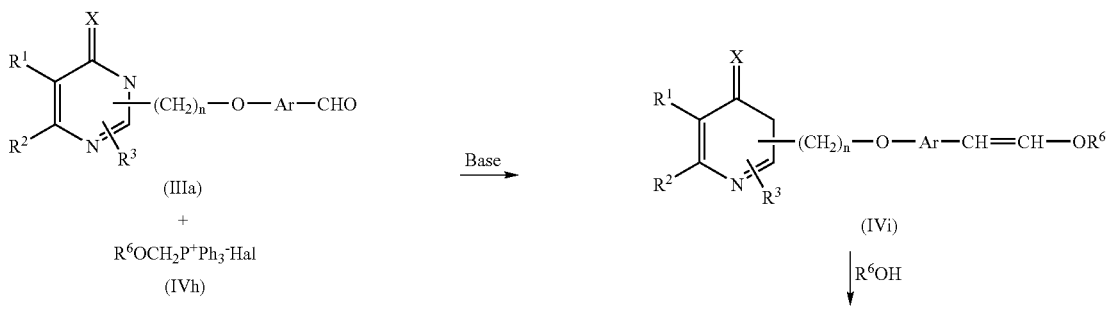

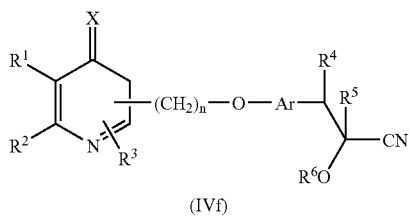

(IVf)

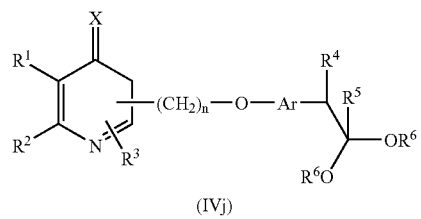

(IVj)

The reaction of a compound of formula (IIIa) where all symbols are as defined earlier with a compound of formula (IVh) where $R^6$ is as defined earlier excluding hydrogen and Hal represent a halogen atom such as Cl, Br, I to produce a compound of formula (IVi) where all symbols are defined earlier and $R^6$ is as defined earlier excluding hydrogen may be carried out under conventional conditions in the presence of a base. The base is not critical. Any base normally employed for Wittig reaction may be employed, metal hydride such as NaH, KH, metal alkoxides such as NaOMe, K$^t$BuO$^-$, NaOEt, metal amides such as LiNH$_2$, LiN(iPr)$_2$. Aprotic solvent such as THF, DMSO, dioxane, DME and the like may be used. Mixture of solvents may be used. HMPA may be used as cosolvent. Inert atmosphere may be employed such as argon and the reaction is more effective under anhydrous conditions. Temperature in the range of −80° C. to 100° C. may be used.

The compound of formula (IVi) where all symbols are as defined earlier and $R^6$ is as defined earlier excluding hydrogen may be converted to a compound of formula (IVj) where $R^4$ and $R^5$ represent hydrogen atoms, $R^6$ is as defined earlier excluding hydrogen and all other symbols are as defined earlier, by treating with an alcohol under anhydrous conditions in the presence of a strong anhydrous acid such as p-toluenesulfonic acid.

The compound of formula (IVj) defined above upon treatment with trialkylsilyl cyanide such as trimethylsilyl cyanide produces a compound of formula (IVf) where $R^4$ and $R^5$ represent hydrogen atoms, $R^6$ is as defined earlier excluding hydrogen and all other symbols are as defined earlier.

In still another embodiment of the present invention there is provided the novel intermediates of formula (IVg)

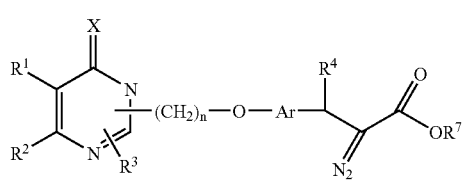

(IVg)

where X represents O or S; the groups $R^1$, $R^2$ and the group $R^3$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^3$ when attached to nitrogen atom represents hydrogen, hydroxy, formyl or substituted or unsubstituted groups selected from alkyl, cycloalkyl, alkoxy, cycloalkoxy, aryl, aralkyl, aryloxy, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives or sulfonic acid derivatives; the linking group represented by —(CH$_2$)$_n$—O— may be attached either through nitrogen atom or through carbon atom where n is an integer ranging from 1–4; Ar represents a substituted or unsubstituted, divalent, single or fused, aromatic or heterocyclic group; $R^4$ represents hydrogen atom, halogen, hydroxy, lower alkyl, alkoxy or substituted or unsubstituted aralkyl group; $R^7$ may be hydrogen or substituted or unsubstituted groups selected from alkyl, cycloalkyl, aryl, aralkyl, heterocyclyl, heteroaryl or heteroaralkyl groups and a process for its preparation and its use in the preparation of β-aryl-α-oxysubstituted alkylcarboxylic acids is provided.

The compound of formula (IVg) where all other symbols are as defined earlier may be prepared by reacting a compound of formula (IVk)

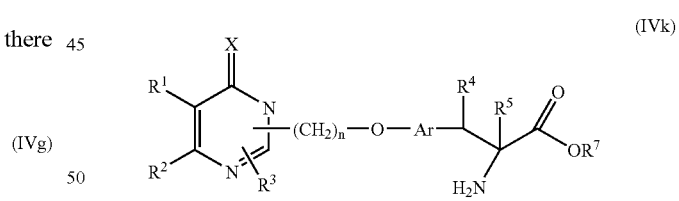

(IVk)

where $R^5$ is hydrogen atom and all other symbols are as defined earlier, with an appropriate diazotizing agent.

The diazotization reaction may be under conventional conditions. A suitable diazotizing agent is an alkyl nitrile, such as iso-amyl nitrile. The reaction may be carried out in presence of solvents such as THF, dioxane, ether, benzene and the like or a combination thereof. Temperature in the range of −50° C. to 80 may be used. The reaction may be carried out in an inert atmosphere which may be maintained by using inert gases such as N$_2$, Ar or He. The duration of the reaction may range from 1 to 24 h, preferably, 1 to 12 h.

The compound of formula (IVk) may also be prepared by a reaction between (IIIh) where all symbols are as defined earlier and a compound of formula (IVl)

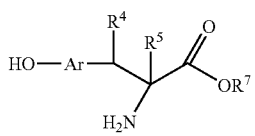

where $R^5$ is hydrogen atom and all other symbols are as defined earlier.

The reaction of compound of formula (IIIh) where all symbols are as defined earlier and a compound of formula (IVl) where all symbols are as defined earlier may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. Acetone may be used as a solvent when $K_2CO_3$ or $Na_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours.

In another embodiment of the present invention there is provided the novel intermediate of formula (IIIm)

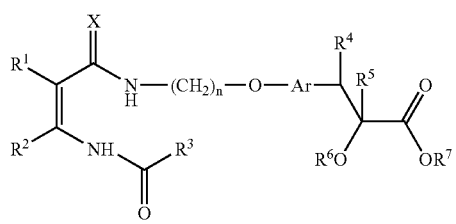

where X represents O or S; the groups $R^1$ and $R^2$ may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^3$ represents hydrogen, hydroxy, formyl or substituted or unsubstituted groups selected from alkyl, cycloalkyl, alkoxy, cycloalkoxy, aryl, aralkyl, aryloxy, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxyalkyl, aryloxyalkyl, aralkoxyalkyl, alkylthio, thioalkyl groups, carboxylic acid derivatives, or sulfonic acid derivatives; n is an integer ranging from 1–4; Ar represents a substituted or unsubstituted, divalent, single or fused, aromatic or heterocyclic group; $R^4$ represents hydrogen atom, halogen, hydroxy, lower alkyl, alkoxy, substituted or unsubstituted aralkyl group or forms a bond together with the adjacent group $R^5$; $R^5$ represents hydrogen, hydroxy, halogen, lower alkyl, alkoxy, acyl, substituted or unsubstituted aralkyl or $R^5$ forms a bond together with $R^4$; $R^6$ may be hydrogen atom or substituted or unsubstituted groups selected from alkyl, acyl, cycloalkyl, aryl, aralkyl, heterocyclyl, heteroaryl, heteroaralkyl, alkoxyalkyl, alkoxycarbonyl, aryloxycarbonyl, alkylaminocarbonyl, or arylaminocarbonyl groups; $R^7$ may be hydrogen or substituted or unsubstituted groups selected from alkyl, cycloalkyl, aryl, aralkyl, heterocyclyl, heteroaryl or heteroaralkyl groups and a process for its preparation and its use in the preparation of β-aryl-α-oxysubstituted alkylcarboxylic acids is provided.

The compound of formula (IIIm) where all symbols are as defined earlier may be prepared by reacting a compound of formula (IIIn)

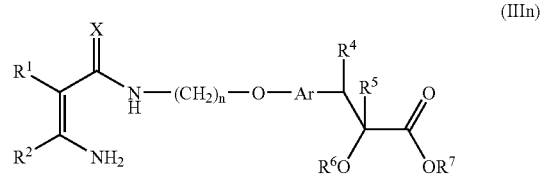

where all symbols are as defined earlier, with a compound of formula (IIIo)

where $L^2$ is halogen, —OH, —$OR^{10}$, —O—C(=O)—$OR^{10}$, where $R^{10}$ is ($C_1$–$C_5$)alkyl and $R^3$ is as defined earlier.

The reaction of compound of general formula (IIIn), where $R^7$ is as defined earlier excluding hydrogen and all other symbols are as defined above with a compound of formula (IIIo) where all symbols are as defined above to produce a compound of general formula (IIIm), all symbols are as defined above may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar or He. The reaction may be carried out at a temperature in the range of –10° C. to 80° C., preferably at a temperature in the range of 0° C. to 60° C. The reaction may be effected in the presence or in absence of a base or an acid. The nature of the base or the acid is not critical. Bases such as pyridine, lutidine, triethyl amine, diisopropylethyl amine and the like, and acids such as AcOH, $C_2H_5COOH$, butyric acid, trifluoroacetic acid, p-toluenesulfonic acid, benzenesulfonic acid and the like, may be used. The duration of the reaction may range from 0.25 to 24 hours, preferably from 0.50 to 6 hours.

In yet another embodiment of the present invention there is provided the novel intermediate of formula (IIIn)

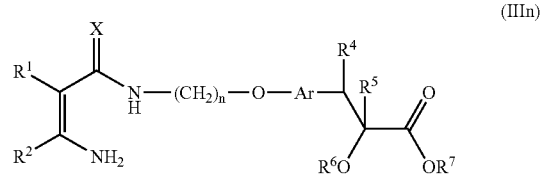

where X represents O or S; the groups $R^1$ and $R^2$ may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; n is an integer ranging from 1–4; Ar represents a substituted or unsubstituted, divalent, single or fused, aromatic or heterocyclic group; $R^4$ represents hydrogen atom, halogen, hydroxy, lower alkyl, alkoxy, substituted or unsubstituted aralkyl group or forms a bond together with the adjacent group $R^5$; $R^5$ represents hydrogen, hydroxy, halogen, lower alkyl, alkoxy, acyl, substituted or unsubstituted aralkyl or $R^5$ forms a bond together with $R^4$; $R^6$ may be hydrogen atom or substituted or unsubstituted groups selected from alkyl, acyl, cycloalkyl, aryl, aralkyl, heterocyclyl, heteroaryl, heteroaralkyl, alkoxyalkyl, alkoxycarbonyl, aryloxycarbonyl, alkylaminocarbonyl, or arylalinocarbonyl groups; $R^7$ may be hydrogen or substituted or unsubstituted groups selected from alkyl, cycloalkyl, aryl, aralkyl, heterocyclyl, heteroaryl or heteroaralkyl groups and a process for its preparation and its use in the preparation of β-aryl-α-oxysubstituted alkylcarboxylic acids is provided.

The compound of formula (IIIn) where all symbols are as defined above may be prepared by reacting a compound of formula (IVm)

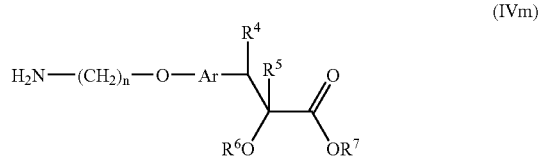

where all symbols are as defined earlier with a compound of formula (IVo)

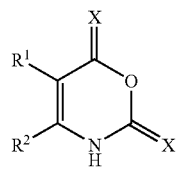

The reaction of compound of formula (IVm) where all symbols are as defined earlier with a compound of formula (IVo) where $R^1$, $R^2$ and X are as defined earlier to produce a compound of formula (IIIn) defined earlier may be carried out neat or in the presence of solvents such as xylene, toluene, dioxane, THF, DMF, DMSO, DME and the like or their mixtures. The reaction may be carried out in an inert atmosphere which is maintained by using inert gases such as $N_2$, Ar or He. The reaction temperature may range from 0° C.–150° C., preferably at a temperature in the range of 0° C.–120° C. The duration of the reaction may range from 0.5 to 12 hours, preferably from 0.5 to 6 hours.

In still another embodiment of the present invention there is provided the novel intermediates of formula (IVn)

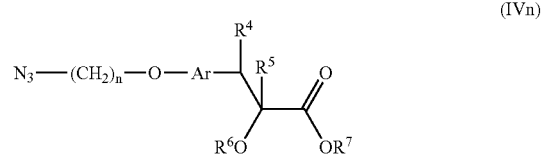

where n is an integer ranging from 1–4; Ar represents a substituted or unsubstituted, divalent, single or fused, aromatic or heterocyclic group; $R^4$ represents hydrogen atom, hydroxy, alkoxy, halogen, lower alkyl, substituted or unsubstituted aralkyl group or forms a bond together with the adjacent group $R^5$; $R^5$ represents hydrogen, hydroxy, alkoxy, halogen, lower alkyl group, acyl, substituted or unsubstituted aralkyl or $R^5$ forms a bond together with $R^4$; $R^6$ may be hydrogen, substituted or unsubstituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, heteroaralkyl groups; $R^7$ may be hydrogen or substituted or unsubstituted groups selected from alkyl, cycloalkyl, aryl, aralkyl, heterocyclyl, heteroaryl, heteroaralkyl groups.

The compound of formula (IVn) may be prepared by treating a compound of general formula (IIId) where all symbols are as defined earlier with appropriate azides such as alkali metal azides like sodium azide, trialkylsilyl azide under conventional conditions. The reaction may be carried out neat or in the presence of solvents such as DMF, acetone, and the like or their mixtures. The reaction temperature may range from 0° C. to 150° C., preferably at a temperature in the range of 25° C. to 100° C. The duration of the reaction may be range from 0.5 to 48 h, preferably from 1 to 12 h.

Alternatively, the compound of general formula (IVn) where $R^4$ and $R^5$ represent a bond and all other symbols are as defined earlier may be prepared by reacting a compound of formula (IIIb)

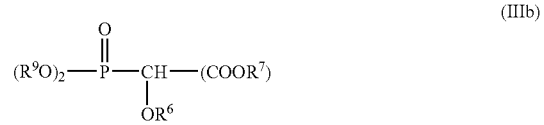

where $R^6$, $R^7$ are as defined earlier excluding hydrogen and $R^9$ represents $(C_1–C_6)$alkyl with a compound of formula (IVp)

where all symbols are as defined earlier, to yield a compound of general formula (IVn) where all symbols are as defined above may be carried out neat in the presence of a base such as alkali metal hydrides like NaH, KH or organolithiums like $CH_3Li$, BuLi and the like or alkoxides such as NaOMe, NaOEt, $BuO^-K^+$ or mixtures thereof. The reaction may be carried out in the presence of solvents such as THF, dioxane, DMF, DMSO, DME and the like or mixtures thereof. HMPA may be used as cosolvent. The reaction temperature may range from –78° C. to 50° C., preferably at a temperature in the range of –10° C. to 30° C. The reaction is more effective under anhydrous conditions.

It is appreciated that in any of the above mentioned reactions, any reactive group in the substrate molecule may be protected according to conventional chemical practice. Suitable protecting groups in any of the above mentioned reactions are those used conventionally in the art. The methods of formation and removal of such protecting groups are those conventional methods appropriate to the molecule being protected.

The pharmaceutically acceptable salts are prepared by reacting the compounds of formula (I) or (IIIm) wherever applicable with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphor-sulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^8$ represents OH may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of compounds of general formula (I) or (IIIm) forming part of this invention may be prepared by crystallization of compound of formula (I) or (IIIm) under different conditions. For example, using different solvents commonly used or their mixtures for crystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention also provides a pharmaceutical composition, containing the compounds of the general formula (I) or (IIIm), as defined above, their derivatives, their analogs, their tautomeric forms, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, retinopathy, and nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, xanthoma and for the treatment of cancer. The compounds of the present inventions are useful in the treatment and/or prophylaxis of the above said diseases in combination/concomittant with one or more HMG CoA reductase inhibitors, hypolipidemic/hypolipoproteinemic agents such as fibric acid derivatives, nicotinic acid, cholestyramine, colestipol, or probucol. The compounds of the present invention in combination with HMG CoA reductase inhibitors, hypolipidemic/hypolipoproteinemic agents can be administered together or within such a period to act synergistically. The HMG CoA reductase inhibitors may be selected from those used for the treatment or prevention of hyperlipidemia such as lovastatin, provastatin, simvastatin, fluvastatin, atorvastatin, cerivastatin and their analogs thereof. Suitable fibric acid derivative may be gemfibrozil, clofibrate, fenofibrate, ciprofibrate, benzafibrate and their analogs thereof.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The compounds of the formula (I) or (IIIm) as defined above are clinically administered to mammals, including man, via either oral or parenteral routes. Administration by the oral route is preferred, being more convenient and avoiding the possible pain and irritation of injection. However, in circumstances where the patient cannot swallow the medication or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

EXAMPLE 1

(±) Ethyl 2-ethoxy-3-[4-[2-[2-ethyl-6-oxo-4-phenyl-1,6-dihydropyrimidin-1-yl]ethoxy]phenyl]propanoate

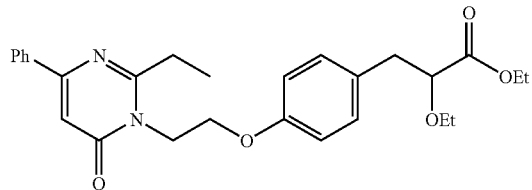

To a stirred suspension of NaH (300 mg, 0.0123 mmol, 60%) in dry DMF (20 mL) at 0° C. was added a solution of (±) 2-ethyl-4-phenyl-1,6-dihydropyrimidin-6-one (1.9 g, 0.0095 mmol) in dry DMF (5 mL). The solution was allowed to stir at room temperature for 20 min. after the effervescence cease. LiBr (1.0 g, 0.012 mmol) was added followed by ethyl 2-ethoxy-3-[4-(2-bromoethoxy)phenyl]propanoate (3.2 g, 0.0095 mmol) (disclosed in U.S. patent application Ser. No. 09/012,585), in dry DMF at room temperature. The reaction mixture was immersed in a preheated oil bath at 80° C. and stirred for 18 h and cooled to room temperature, poured into water and extracted with ethyl acetate (3×10 mL). The combined ethyl acetate layers were washed with brine, dried ($Na_2SO_4$) and concentrated. The crude compound was chromatographed over silica gel using ethyl acetate:per. ether (3:7) to yield the title compound as a liquid (900 mg, 21%).

$^1$H NMR ($CDCl_3$): δ 8.01–7.98 (m, 2H), 7.50–7.43 (m, 3H), 7.12 (d, J=8.31 Hz, 2H), 6.78 (s, 1H), 6.75 (d, J=8.31 Hz, 2H), 4.47 (t, J=4.89 Hz, 2H), 4.30 (t, J=4.89 Hz, 2H), 4.15 (q, J=7.15 Hz, 2H), 3.93 (t, J=6.65 Hz, 1H), 3.62–3.26 (m, 2H), 3.12 (q, J=7.29 Hz, 2H), 2.90 (d, J=6.65 Hz, 2H), 1.45 (t, J=7.29 Hz, 3H), 1.25–1.09 (m, 6H).

The compounds given in Table 1 were also prepared using a similar method described in Example 1:

TABLE 1

| Example No. | Structure | mp or nature | Yield | $^1$H NMR ($CDCl_3$):δ |
|---|---|---|---|---|
| 2 | 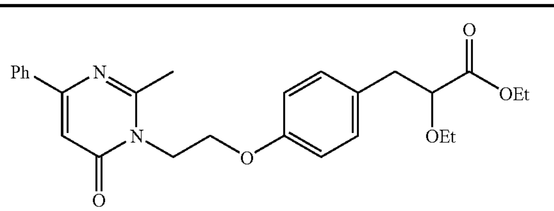 | Liquid | 39% | 7.95–7.92 (m, 2H), 7.46–7.43 (m, 3H), 7.12 (d, J=8.39 Hz, 2H), 6.79–6.75 (m, 3H), 4.46 (t, J=4.56 Hz, 2H), 4.31 (t, J=4.56 Hz, 2H), 4.18 (q, J=7.15 Hz, 2H), 3.92 (t, J=6.32 Hz, 1H), 3.65–3.26 (m, 2H), 2.92 (d, J=6.32 Hz, 2H), 2.82 (s, 3H), 1.36–1.13 (m, 6H). |
| 3 | 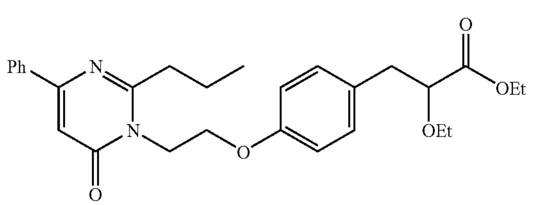 | Liquid | 18% | 8.05–7.97 (m, 2H), 7.47–7.43 (m, 3H), 7.15–7.11 (d, J=8.40 Hz, 2H), 6.79–6.75 (m, 3H), 4.50–4.47 (t, J=4.70 Hz, 2H), 4.30 (t, J=4.70 Hz, 2H), 4.17 (q, J=7.15 Hz, 2H), 3.93 (t, J=6.55 Hz, 1H), 3.60–3.20 (m, 2H), 3.03 (t, J=7.15 Hz, 2H), 2.92 (d, J=6.55 Hz, 2H), 1.96 (q, J=7.47 Hz, 2H), 1.25–1.08 (m, 9H). |
| 4 | 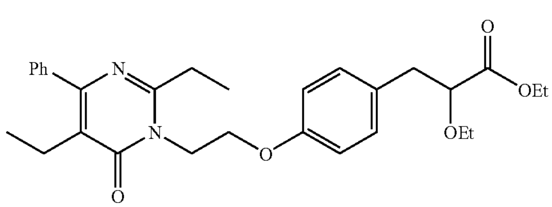 | White solid | 40% | 7.60–7.40 (m, 5H), 7.13 (d, J=8.30 Hz, 2H), 6.78 (d, J=8.30 Hz, 2H), 4.46 (t, J=4.98 Hz, 2H), 4.31 (t, J=4.98 Hz, 2H), 4.15 (q, J=7.06 Hz, 2H), 3.94 (t, J=6.65 Hz, 1H), 3.70–3.25 (m, 2H), 3.02 (q, J=7.47 Hz, 2H), 2.93 (d, J=6.65 Hz, 2H), 2.52 (q, J=7.15 Hz, 2H), 1.50–1.15 (m, 12H). |

TABLE 1-continued

| Example No. | Structure | mp or nature | Yield | ¹H NMR (CDCl₃):δ |
|---|---|---|---|---|
| 5 | 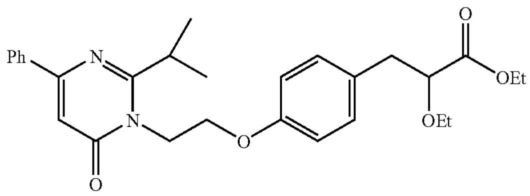 | Liquid | 10% | 8.03–7.95 (m, 2H), 7.50–7.40 (m, 3H), 7.12 (d, J=8.30 Hz, 2H), 6.76 (s, 1H), 6.75 (d, J=8.30 Hz, 2H), 4.51 (t, J=4.98 Hz, 2H), 4.27 (t, J=4.98 Hz, 2H), 4.14 (q, J=7.15 Hz, 2H), 3.92 (t, J=6.74 Hz, 1H), 3.70–3.20 (m, 2H), 3.16–3.00 (m, 1H), 2.91 (d, J=6.74 Hz, 2H), 1.42 (s, 3H), 1.40 (s, 3H), 1.30–1.14 (m, 6H). |
| 6 | 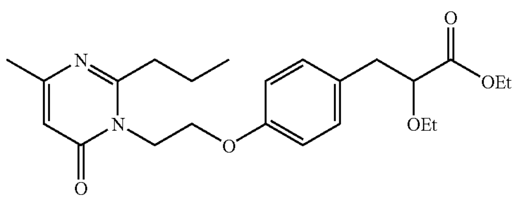 | Gummy liquid | 25% | 7.12 (d, J=8.70 Hz, 2H), 6.75 (d, J=8.70 Hz, 2H), 6.18 (s, 1H), 4.38 (t, J=5.00 Hz, 2H), 4.22 (t, J=5.00 Hz, 2H), 4.15 (q, J=10.50 Hz, 2H), 3.94 (t, J=7.00 Hz, 1H), 3.65–3.20 (m, 2H), 3.00–2.85 (m, 4H), 2.21 (s, 3H), 1.90–1.70 (m, 2H), 1.30–1.00 (m, 9H). |
| 7 | 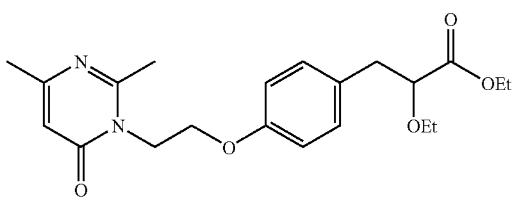 | Colorless liquid | 32% | 7.15 (d, J=8.62 Hz, 2H), 6.85 (d, J=8.62 Hz, 2H), 6.40 (s, 1H), 4.68 (t, J=4.77 Hz, 2H), 4.27 (t, J=4.77 Hz, 2H), 4.16 (q, J=7.35 Hz, 2H), 3.95 (t, J=6.61 Hz, 1H), 3.70–3.25 (m, 2H), 2.95 (d, J=6.61 Hz, 2H), 2.57 (s, 3H), 2.39 (s, 3H), 1.35–1.10 (m, 6H). |
| 8 | 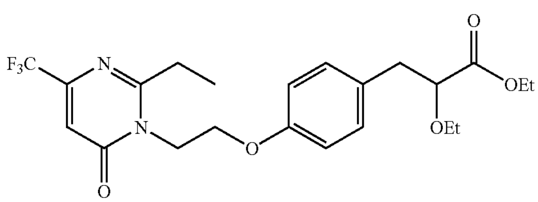 | Liquid | 21% | 7.13 (d, J=8.45 Hz, 2H), 6.74 (d, J=8.45 Hz, 2H), 6.69 (s, 1H), 4.46 (t, J=4.77 Hz, 2H), 4.27 (t, J=4.77 Hz, 2H), 4.15 (q, J=7.15 Hz, 2H), 3.93 (t, J=6.48 Hz, 1H), 3.62–3.20 (m, 2H), 3.12 (q, J=7.26 Hz, 2H), 2.92 (d, J=6.48 Hz, 2H), 1.40–1.10 (m, 9H). |
| 9 | 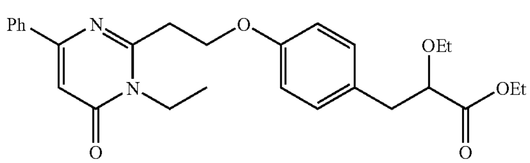 | Liquid | 14% | 8.04–7.99 (m, 2H), 7.49–7.46 (m, 3H), 7.14 (d, J=8.62 Hz, 2H), 6.93 (s, 1H), 6.86 (d, J=8.62 Hz, 2H), 4.56–4.40 (m, 4H), 4.18 (q, J=7.15 Hz, 2H), 3.97 (t, J=6.62 Hz, 1H), 3.65–3.25 (m, 4H), 2.94 (d, J=6.62 Hz, 2H), 1.42 (t, J=7.10 Hz, 3H), 1.25–1.10 (m, 6H). |
| 10 | 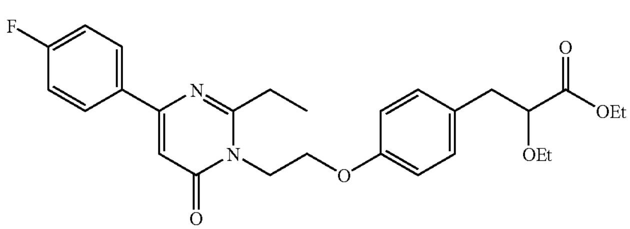 | Gummy liquid | 25% | 8.10–7.97 (m, 2H), 7.20–7.10 (m, 2H), 7.12 (d, J=8.49 Hz, 2H), 6.75 (d, J=8.49 Hz, 2H), 6.72 (s, 1H), 4.47 (t, J=4.77 Hz, 2H), 4.29 (t, J=4.77 Hz, 2H), 4.15 (q, J=7.15 Hz, 2H), 3.92 (t, J=6.46 Hz, 1H), 3.65–3.20 (m, 2H), 3.09 (q, J=7.47 Hz, 2H), 2.92 (d, J=6.46 Hz, 2H), 1.44 (t, J=7.47 Hz, 3H), 1.30–1.10 (m, 6H). |

TABLE 1-continued

| Example No. | Structure | mp or nature | Yield | $^1$H NMR (CDCl$_3$):δ |
|---|---|---|---|---|
| 11 | 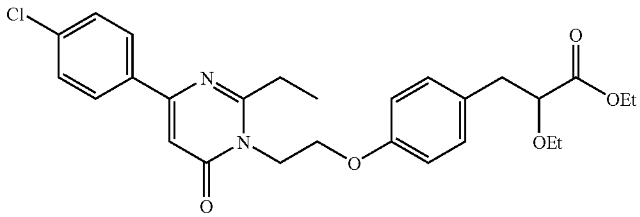 | Gummy liquid | 22% | 7.94 (d, J=8.40 Hz, 2H), 7.41 (d, J=8.40 Hz, 2H), 7.12 (d, J=8.40 Hz, 2H), 6.75 (d, J=8.40 Hz, 2H), 6.74 (s, 1H), 4.46 (t, J=4.66 Hz, 2H), 4.28 (t, J=4.66 Hz, 2H), 4.15 (q, J=6.92 Hz, 2H), 3.92 (t, J=6.55 Hz, 1H), 3.65–3.20 (m, 2H), 3.09 (q, J=7.47 Hz, 2H), 2.91 (d, J=6.55 Hz, 2H), 1.45 (t, J=7.24 Hz, 3H), 1.30–1.10 (m, 6H). |
| 12 | 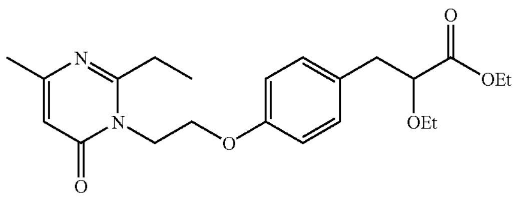 | liquid | 59% | 7.16 (d, J=8.62 Hz, 2H), 6.86 (d, J=8.62 Hz, 2H), 6.43 (s, 1H), 4.70 (t, J=4.77 Hz, 2H), 4.28 (t, J=4.77 Hz, 2H), 4.17 (q, J=7.11 Hz, 2H), 3.96 (t, J=6.55 Hz, 1H), 3.70–3.50 (m, 1H), 3.42–3.22 (m, 1H), 2.95 (d, J=6.55 Hz, 2H), 2.83 (q, J=7.60 Hz, 2H), 2.40 (s, 3H), 1.32 (t, J=7.60 Hz, 3H), 1.23 (t, J=7.11 Hz, 3H), 1.63 (t, J=6.90 Hz, 3H). |

EXAMPLE 13

(±) 2-Ethoxy-3-[4-[2-[2-ethyl-6-oxo-4-phenyl-1,6-dihydropyrimidin-1-yl]ethoxy]phenyl]propanoic acid

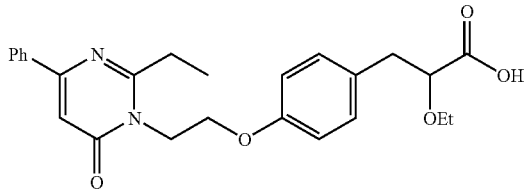

To the methanolic (15 mL) solution of (±) ethyl-2-ethoxy-3-[4-[2-ethyl-6-oxo-4-phenyl-1,6-dihydropyrimidin-1-yl]ethoxy]phenyl]propanoate (420 mg, 0.909 mmol) obtained in example 1 was added NaOH (365 mg, 9.125 mmol) in H$_2$O (10 mL), the mixture was stirred at 25° C. for 1 hr, evaporated the solvent under reduced pressure. The residue was added to 50 mL of cold water and washed with ethyl acetate (2×50 mL). The aqueous layer was acidified with 2N HCl and extracted with ethyl acetate (3×100 mL). The combined ethyl acetate layers were washed with water, brine, dried (Na$_2$SO$_4$) and evaporated the solvent, to give a stick compound, which was solidified by either long drying under vacuum or trituration with dry ether to give a white solid (380 mg, 96%) mp: 138–140° C.

$^1$H NMR (CDCl$_3$): δ 8.03–7.98 (m, 2H), 7.47–7.44 (m, 3H), 7.13 (d, J=8.63 Hz, 2H), 6.81 (s, 1H), 6.76 (d, J=8.63 Hz, 2H), 4.46 (t, J=4.98 Hz, 2H), 4.31 (t, J=4.98 Hz, 2H), 4.09–3.95 (m, 1H), 3.65–3.35 (m, 2H), 3.15–2.85 (m, 4H), 1.46 (t, J=7.29 Hz, 3H), 1.18 (t, J=7.06 Hz, 3H).

The compounds given in Table 2 were also prepared using a similar method described in Example 14:

TABLE 2

| Example No. | Structure | mp or nature | Yield | $^1$H NMR (CDCl$_3$):δ |
|---|---|---|---|---|
| 14 | 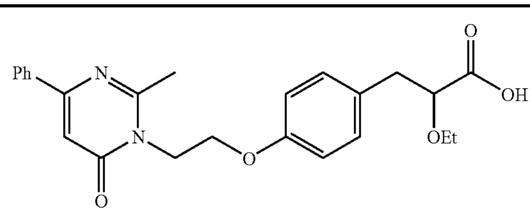 | White hygroscopic solid 108–110° C. | 56% | 7.97–7.93 (m, 2H), 7.47–7.44 (m, 3H), 7.14 (d, J=8.63 Hz, 2H), 6.80 (d, J=8.63 Hz, 2H), 6.78 (s, 1H), 4.48 (t, J=4.50 Hz, 2H), 4.31 (t, J=4.50 Hz, 2H), 4.05–3.99 (m, 1H), 3.56–3.43 (m, 2H), 3.05 (dd, J=4.24 Hz and 14.12 Hz, 1H), 2.92 (dd, J=7.48 Hz and 14.12 Hz, 1H), 2.82 (s, 3H), 1.16 (t, 6.92 Hz, 3H) |

TABLE 2-continued

| Example No. | Structure | mp or nature | Yield | $^1$H NMR (CDCl$_3$):δ |
|---|---|---|---|---|
| 15 | 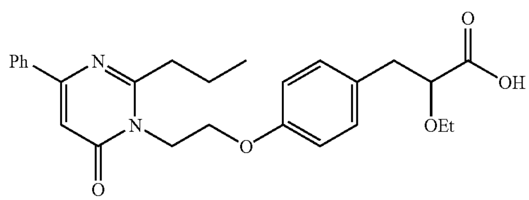 | White solid 132–134° C. | 30% | 8.01–7.90 (m, 2H), 7.50–7.40 (m, 3H), 7.15 (d, J=8.30 Hz, 2H), 6.81 (s, 1H), 6.79 (d, J=8.30 Hz, 2H), 4.49 (t, J=4.67 Hz, 2H), 4.32 (t, J=4.67 Hz, 2H), 4.10–3.90 (m, 1H), 3.70–3.30 (m, 2H), 3.15–2.80 (m, 4H), 1.98 (q, J=7.58 Hz, 2H), 1.40–1.10 (m, 6H) |
| 16 | 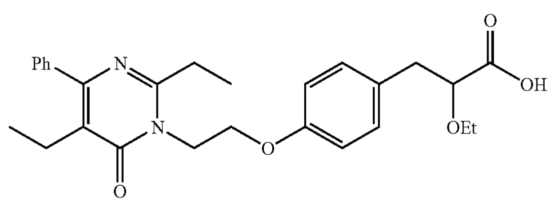 | White solid | 54% | 7.55–7.40 (m, 5H), 7.14 (d, J=8.31 Hz, 2H), 6.80 (d, J=8.31 Hz, 2H), 4.47 (t, J=4.77 Hz, 2H), 4.32 (t, J=4.77 Hz, 2H), 4.10–4.00 (m, 1H), 3.70–3.40 (m, 2H), 3.10–2.90 (m, 4H), 2.52 (q, J=7.38 Hz, 2H), 1.35 (t, J=7.25 Hz, 3H), 1.25–1.10 (m, 6H) |
| 17 | 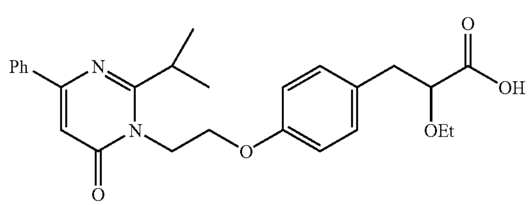 | White solid 82–84° C. | 27% | 8.04–8.01 (m, 2H), 7.48–7.45 (m, 3H), 7.15 (d, J=8.53 Hz, 2H), 6.84 (s, 1H), 6.77 (d, J=8.53 Hz, 2H), 4.55 (t, J=4.77 Hz, 2H), 4.29 (t, J=4.77 Hz, 2H), 4.04–3.98 (m, 1H), 3.76–3.36 (m, 3H), 3.05 (dd, J=4.25 and 13.70 Hz, 1H), 2.95 (dd, J=6.13 and 13.70 Hz, 1H), 1.44 (s, 3H), 1.41 (s, 3H), 1.16 (t, J=6.82 Hz, 3H) |
| 18 | 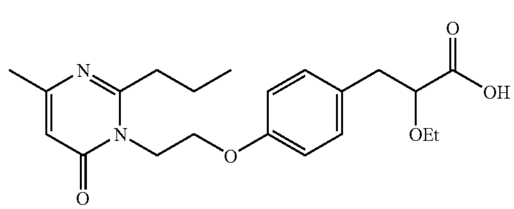 | White solid 106–110° C. | 79% | 7.13 (d, J=8.39 Hz, 2H), 6.74 (d, J=8.39 Hz, 2H), 6.20 (s, 1H), 4.41 (t, J=4.78 Hz, 2H), 4.25 (t, J=4.78 Hz, 2H), 4.04–3.98 (m, 1H), 3.65–3.30 (m, 2H), 3.10–2.85 (m, 4H), 2.23 (s, 3H), 1.90–1.65 (m, 2H), 1.15 (t, J=7.04 3H), 105 (t, J=7.40 Hz, 3H) |

TABLE 2-continued

| Example No. | Structure | mp or nature | Yield | $^1$H NMR (CDCl$_3$):δ |
|---|---|---|---|---|
| 19 | 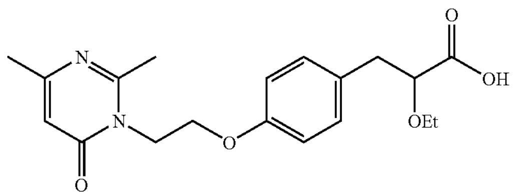 | White fluffy hygroscopic solid 126–128° C. | 34% | 7.16 (d, J=8.63 Hz, 2H), 6.84 (d, J=8.63 Hz, 2H), 6.47 (s, 1H), 4.71 (t, J=4.60 Hz, 2H), 4.27 (t, J=4.60 Hz, 2H), 4.07–4.01 (m, 1H), 3.65–3.38 (m, 2H), 3.08 (dd, J=4.34 and 14.12 Hz, 1H), 2.95 (dd, J=6.74 and 14.12 Hz, 1H), 2.62 (s, 3H), 2.45 (s, 3H), 1.18 (t, J=7.00 Hz, 3H) |
| 20 | 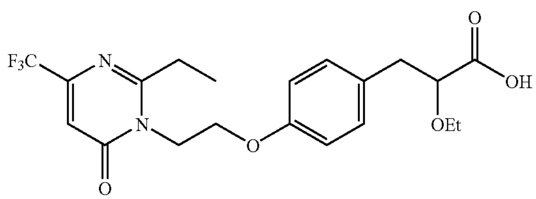 | White solid 124–126° C. | 58% | 7.13 (d, J=8.39 Hz, 2H), 6.75 (d, J=8.39 Hz, 2H), 6.70 (s, 1H), 4.46 (t, J=4.65 Hz, 2H), 4.27 (t, J=4.65 Hz, 2H), 4.06–4.00 (m, 1H), 3.60–3.40 (m, 2H), 3.20–2.90 (m, 4H), 1.38 (t, J=7.40 Hz, 3H), 1.18 (t, J=7.00 Hz, 3H) |
| 21 | 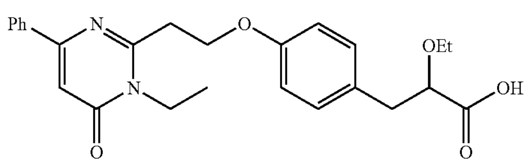 | Colorless liquid | 41% | 8.10–7.95 (m, 2H), 7.55–7.40 (m, 3H), 7.13 (d, J=8.63 Hz, 2H), 6.92 (s, 1H), 6.87 (d, J=8.63 Hz, 2H), 4.60–4.40 (m, 4H), 4.15–4.00 (m, 1H), 3.70–3.45 (m, 2H), 3.38 (t, J=6.83 Hz, 2H), 3.10 (dd, J=4.15 and 18.58 Hz, 1H), 2.95 (dd, J=7.38 and 18.58 Hz, 1H), 1.41 (t, J=7.05 Hz, 3H), 1.18 (t, J=6.83 Hz, 3H) |
| 22 | 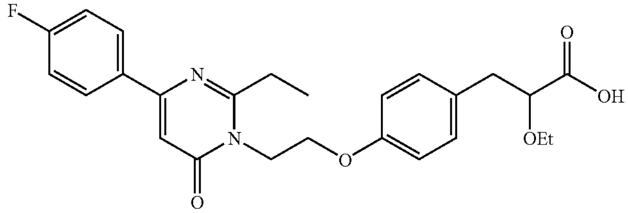 | White solid 110–114° C. | 54% | 8.10–7.90 (m, 2H), 7.20–7.10 (m, 2H), 7.12 (d, J=8.64 Hz, 2H), 6.76 (d, J=8.64 Hz, 2H), 6.73 (s, 1H), 4.47 (t, J=4.31 Hz, 2H), 4.30 (t, J=4.31 Hz, 2H), 4.10–3.98 (m, 1H), 3.62–3.35 (m, 2H), 3.15–2.85 (m, 4H), 2.00 (bs, D$_2$O exchangeable, 1H,), 1.44 (t, J=7.38 Hz, 3H), 1.16 (t, J=6.96 Hz, 3H) |

TABLE 2-continued

| Example No. | Structure | mp or nature Yield | $^1$H NMR (CDCl$_3$):δ |
|---|---|---|---|
| 23 | 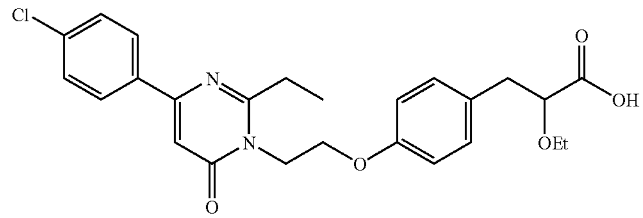 | Pale yellow solid 62–64° C. 68% | 7.95 (d, J=8.63 Hz, 2H), 7.42 (d, J=8.54 Hz, 2H), 7.13 (d, J=8.63 Hz, 2H), 6.77 (d, J=8.54 Hz, 2H), 6.75 (s, 1H), 4.47 (t, J=4.80 Hz, 2H), 4.30 (t, J=4.80 Hz, 2H), 4.10–3.95 (m, 1H), 3.65–3.35 (m, 2H), 3.15–2.85 (m, 4H), 1.44 (t, J=7.38 Hz, 3H), 1.16 (t, J=7.01 Hz, 3H) |
| 24 | 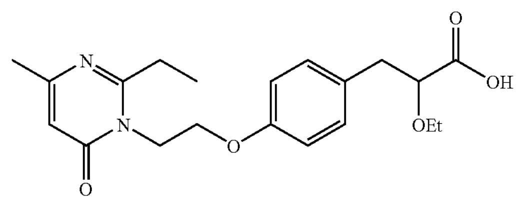 | white solid 100–103° C. 50% | 7.19 (d, J=8.62 Hz, 2H), 6.88 (d, J=8.62 Hz, 2H), 6.45 (s, 1H), 4.73 (t, J=4.79 Hz, 2H), 4.30 (t, J=4.79 Hz, 2H), 4.06 (dd, J=7.28, 4.56 Hz, 1H), 3.70–3.40 (m, 2H), 3.11 (dd, J=14.16, 4.56 Hz, 1H), 2.97 (dd, J=14.16 and 7.28 Hz, 1H), 2.85 (q, J=7.58 Hz, 2H), 2.42 (s, 3H), 1.33 (t, J=7.58 Hz, 3H), 1.20 (t, J=7.01 Hz, 3H). |

EXAMPLE 25

[2R, N(1S)]-2ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide (25a)

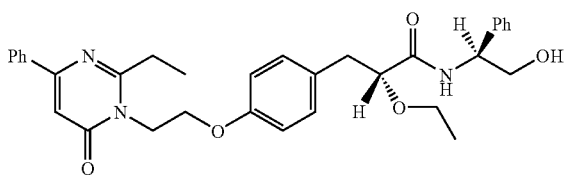

[2S, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide (25b)

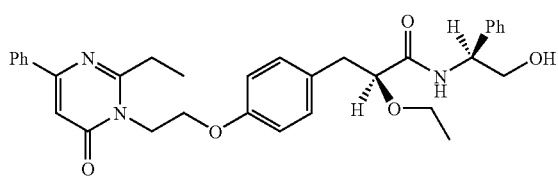

To a solution of (±) 2-ethoxy-3-[4-[2-[2-ethyl-6-oxo-4-phenyl-1,6-dihydropyrimidin-1-yl]ethoxy]phenyl]propanoic acid (1 g, 2.37 mmol) obtained in example 13 in dry dichloromethane (10 mL) was added triethyl amine (600 mg, 5.92 mmol). The reaction mixture was cooled to 0° C. and pivaloyl chloride (314 mg, 2.6 mmol) was added. The reaction mixture was stirred at 25° C. for 0.5 h until all the acid is converted to mixed anhydride, followed by addition of S(+) 2-phenylglycinol (375 mg, 2.6 mmol) and triethyl amine (600 mg, 5.92 mmol) in dry dichloromethane (10 mL). After stirring the reaction mixture at about 25° C. for 2 h, water was added and extracted with dichloromethane. The organic extracts were washed with water and brine, dried (Na$_2$SO$_4$) and evaporated. The residue was purified by silica gel column chromatography using a gradient of 50–80% ethyl acetate in pet ether as an eluent to afford a diastereomer tentatively assigned as [2R, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl) propanamide (25a) (400 mg, followed by [2S, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide (25b) as a viscous liquid (400 mg).

25a: [α]$^{25}_D$=18.2 (c=1.0, CHCl$_3$) 98% d.e (by HPLC); $^1$H NMR (CDCl$_3$) δ: 8.10–7.95 (m, 2H), 7.60–7.40 (m, 3H), 7.25 (d, J=8.30 Hz, 2H), 7.10–7.00 (m, 5H), 6.81 (s, 1H), 6.70(d, J=8.30 Hz, 2H), 4.99–4.96 (m, 1H), 4.42 (t, J=4.60 Hz, 2H), 4.25 (t, J=4.60 Hz, 2H), 4.00–3.92 (m, 1H), 3.80 (d, J=4.66 Hz, 2H), 3.60–3.40 (m, 2H), 3.13 (q, J=7.38 Hz, 2H), 3.02 (dd, J=3.32 Hz and 13.33 Hz, 1H), 2.85 (dd, J=6.74 Hz and 13.33 Hz, 1H), 1.47 (t, J=7.38 Hz, 3H), 1.16 (t, J=7.00 Hz, 3H).

25b: viscous liquid, $[\alpha]^{25}_D$=−16.0 (c=1.0, CHCl₃) 98.5% d.e (by HPLC); ¹H NMR (CDCl₃) δ: 8.00–7.90 (m, 2H), 7.56–7.40 (m, 3H), 7.25 (d, J=8.27 Hz, 2H), 7.05–6.95 (m, 5H), 6.80 (s, 1H), 6.67(d, J=8.27 Hz, 2H), 4.95–4.90 (m, 1H), 4.38 (t, J=4.60 Hz, 2H), 4.22 (t, J=4.60 Hz, 2H), 4.00–3.90 (m, 1H), 3.88 (d, J=4.64 Hz, 2H), 3.60–3.40 (m, 2H), 3.10 (q, J=7.42 Hz, 2H), 3.00 (dd, J=4.30 Hz and 13.42 Hz, 1H), 2.85 (dd, J=6.72 Hz and 13.42 Hz, 1H), 1.50 (t, J=7.40 Hz, 3H), 1.18 (t, J=7.02 Hz, 3H).

EXAMPLE 26

(−) 2-Ethoxy-3-[4-[2-[2-ethyl-6-oxo-4-phenyl-1,6-dihydropyrimidin-1-yl]ethoxyl]phenyl]propanoic acid

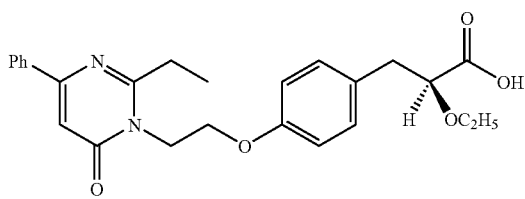

A solution of [2S, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethyl)propanamide (295 mg, 0.53 mmol) obtained in example 25 in a mixture of 1M sulfuric acid (7.7 mL) and dioxane/water (1:1, 14 mL) was heated at 90° C. for 48 h and the pH of the mixture was adjusted to 4 by the addition of aqueous sodium bicarbonate solution. The mixture was extracted with ethyl acetate and the combined ethyl acetate layers were washed with water, brine, dried (Na₂SO₄) and evaporated to yield a colorless solid (43%) mp 140–142° C.

$[\alpha]^{25}_D$=−9.2; ¹H NMR (CDCl₃): δ 8.05–7.95 (m, 2H), 7.52–7.40 (m, 3H), 7.13 (d, J=8.40 Hz, 2H), 6.80 (s, 1H), 6.78 (d, J=8.40 Hz, 2H), 4.49 (t, J=4.71 Hz, 2H), 4.31 (t, J=4.71 Hz, 2H), 4.10–4.00 (m, 1H), 3.65–3.35 (m, 2H), 3.12 (q, J=7.15 Hz, 2H), 3.01 (dd, J=4.66 Hz and 11.2 Hz, 1H), 2.95 (dd, J=9.2 Hz, 14.2 Hz, 1H), 2.00 (bs, D₂O exchangeable 1H), 1.46 (t, J=7.15 Hz, 3H), 1.16 (t, J=6.92 Hz, 3H).

EXAMPLE 27

(+) 2-Ethoxy-3-[4-[2-[2-ethyl-6-oxo-4-phenyl-1,6-dihydropyrimidin-1-yl]ethoxy]phenyl]propanoic acid

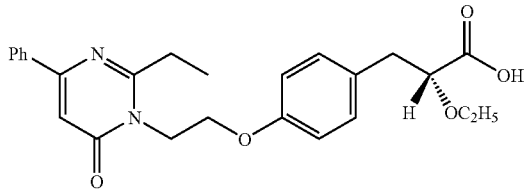

The title compound (28%) was prepared from a solution of [2R, N(1S)]-2-ethoxy-3-[4-[2-[2-ethyl-6-oxo-4-phenyl-1,6-dihydropyrimidin-1-yl]ethoxy]phenyl]-N-(2-hydroxy-1-phenylethly)propanamide obtained in example 25 (223 mg, 0.540 mmol) by a similar method as described in example 26, mp 145–147° C.

$[\alpha]^{25}_D$=+11.00; ¹H NMR (CDCl₃): δ 8.02–7.97 (m, 2H), 7.50–7.40 (m, 3H), 7.15 (d, J=8.54 Hz, 2H), 6.81 (s, 1H), 6.80 (d, J=8.54 Hz, 2H), 4.50 (t, J=4.88 Hz, 2H), 4.33 (t, J=4.88 Hz, 2H), 4.10–4.00 (m, 1H), 3.60–3.40 (m, 2H), 3.12 (q, J=7.32 Hz, 2H), 3.07 (d, J=3.91 Hz and 13.43 Hz, 1H), 2.95 (dd, J=7.32 Hz and 13.43 Hz and 1H), 2.00 (bs, D₂O exchangeable, 1H), 1.48 (t, J=7.32 Hz, 3H), 1.18 (t, J=6.83 Hz, 3H).

EXAMPLE 28

(±) 2-Ethoxy-3-[4-[2-[2-methyl-6-oxo-4-phenyl-1,6-dihydropyrimidin-1-yl]ethoxy]phenyl]propanoic acid, magnesium salt

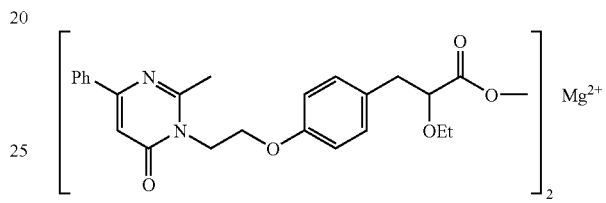

To a stirred solution of (±) 2-ethoxy-3-[4-[2-[2-methyl-6-oxo-4-phenyl-1,6-dihydropyrimidin-1-yl]ethoxy]phenyl] propanoic acid obtained in example 14 (100 mg, 0236 mmol) in dry methanol (5 mL) magnesium hydroxide (6.5 mg, 0.168 mmol) was added and allowed to stir at room temperature for 24 h. The solvent was evaporated and triturated with dry ether, dried over CaCl₂ to yield the title compound as a white solid (100 mg, 99%), mp 158–160° C.

¹H NMR: δ 7.93–7.90 (m, 2H), 7.40–7.37 (m, 3H), 7.07 (d, J=8.30 Hz, 2H), 6.73 (d, J=8.30 Hz, 2H), 6.71 (s, 1H), 4.60–4.30 (m, 3H), 4.25 (t, J=4.56 Hz, 2H), 3.80–3.40 (m, 2H), 3.20–2.80 (m, 2H), 2.77 (s, 3H), 1.00 (t, J=7.60 Hz, 3H).

EXAMPLE 29

(±) 2-Ethoxy-3-[4-[2-[2-methyl-6-oxo-4-phenyl-1,6-dihydropyrimidin-1-yl]ethoxy]phenyl]propanoic acid, sodium salt

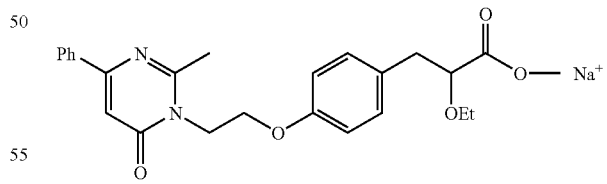

To a stirred solution of (±) 2-ethoxy-3-[4-[2-[2-methyl-6-oxo-4-phenyl-1,6-dihydropyrimidin-1-yl]ethoxy]phenyl] propanoic acid obtained in example 14 (100 mg, 0.236 mmol) in dry methanol (1.5 mL) sodium methoxide (12.8 mg, 0.236 mmol) in methanol (1.5 mL) was added and allowed to stir at room temperature for 12 h. The solvent was evaporated and washed with 10% methanol in ether solution (3×5 mL) and dried under vacuum for 4 h to yield the title compound as a cream colour hygroscopic solid (70mg, 67%), mp 288–292° C.

$^1$H NMR (CD$_3$OD): δ 8.06–7.88 (m, 2H), 7.45–7.30 (m, 3H), 7.10 (d, J=8.54 Hz, 2H), 6.72 (d, J=8.54 Hz, 2H), 6.71 (s, 1H), 4.40 (t, J=4.98 Hz, 2H), 4.24 (t, J=4.98 Hz, 2H), 3.70–3.60 (m, 1H), 3.55–3.35 (m, 1H), 3.26 (s, 3H), 3.20–3.05 (m, 1H), 2.85 (dd, J=4.05 Hz and 14.02 Hz, 1H), 2.65 (dd, J=8.72 Hz and 14.02 Hz, 1H), 0.97 (t, J=7.05 Hz, 3H).

EXAMPLE 30

(±) 2-Ethoxy-3-[4-[2-[2-methyl-6-oxo-4-phenyl-1,6-dihydropyrimidin-1-yl]ethoxy]phenyl]propanoic acid, arginine salt

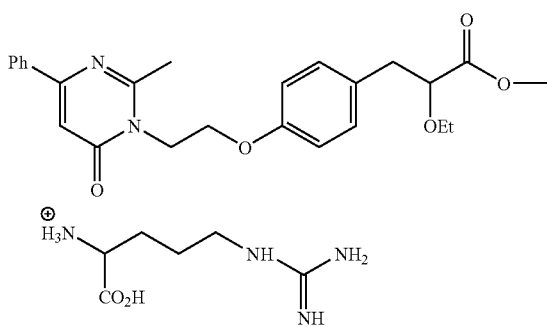

To a stirred solution of (±) 2-ethoxy-3-[4-[2-[2-methyl-6-oxo-4-phenyl-1,6-dihydropyrimidin-1-yl]ethoxy]phenyl] propanoic acid obtained in example 14 (100 mg, 0.24 mmol) in dry methanol (5 mL) L-arginine (40 mg, 0.23 mmol) was added at 25° C. and stirred the reaction mixture over 24 h. The solvent was evaporated at low temperature and triturated with dry ether (3×20 mL) and dried under vacuum at 50° C. for 6 h to yield the title compound as slightly hygroscopic white solid (100 mg, 72%), mp 168–170° C.

$^1$H NMR (CD$_3$OD): δ 8.00–7.85 (m, 2H), 7.40–7.30 (m, 3H), 7.08 (d, J=8.30 Hz, 2H), 6.72 (d, J=8.30 Hz, 2H), 6.70 (s, 1H), 4.41 (t, J=4.77 Hz, 2H), 4.23 (t, J=4.77 Hz, 2H), 3.72–3.60 (m, 1H), 3.55–3.30 (m, 2H), 3.25–3.00 (s, 4H), 2.80 (dd, J=4.06 Hz and 13.72 Hz, 1H), 2.70 (dd, J=9.06 Hz and 13.72 Hz, 1H), 2.71 (s, 3H), 1.90–1.50 (m, 3H), 0.96 (t, J=7.30Hz, 3H).

The compounds of the present invention lowered random blood sugar level, triglyceride, total cholesterol, LDL, VLDL and increased HDL. This was demonstrated by in vitro as well as in vivo animal experiments.

Demonstration of Efficacy of Compounds

A) In vitro:
a) Determination of hPPARα Activity:

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene. 1992. 118: 137–141; Superfect Transfection Reagent Handbook. February 1997. Qiagen, Germany).

b) Determination of hPPARγ Activity:

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 μM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992. 118: 137–141; Guide to Eukaryotic Transfections with Cationic Lipid Reagents. Life Technologies, GIBCO BRL, USA).

| PPARα AND PPARγ ACTIVITY | | | | |
|---|---|---|---|---|
| Example No | Concentration | PPARα | Concentration | PPARγ |
| Example 22 | 50 μM | 7.7 | 1 μM | 23.9 |
| Example 23 | 50 μM | 6.4 | 1 μM | 19.95 | c) Determination of HMG CoA Reductase Inhibition Activity:

Liver microsome bound reductase can be prepared from 2% cholestyramine fed rats at mid-dark cycle. Spectrophotometric assays can be carried out in 100 mM KH$_2$PO4, 4 mM DTT, 0.2 mM NADPH, 0.3 mM HMG CoA and 125 μg of liver microsomal enzyme. Total reaction mixture volume can be kept as 1 ml and the reaction started by addition of HMG CoA. Reaction mixture can be incubated at 37° C. for 30 min and decrease in absorbence at 340 nm can be recorded. Reaction mixture without substrate can be used as blank (Goldstein, J. L and Brown, M. S. Progress in understanding the LDL receptor and HMG CoA reductase, two membrane proteins that regulate the plasma cholesterol. J. Lipid Res. 1984, 25: 1450–1461). This protocol can be used to test for compounds that inhibit HMG CoA reductase enzyme.

B) In vivo:
a) Efficacy in Genetic Models:

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1): 1–6) mice and Zucker fa/fa rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C$_{57}$BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.001 mg to 30 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 μl) through orbital sinus, using heparinised capillary in tubes containing EDTA which was centrifuged to obtain plasma. The plasma glucose and triglyceride levels were measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula given below.

No adverse effects were observed for any of the mentioned compounds of invention in the above test.

BLOOD GLUCOSE LOWERING ACTIVITY IN DB/DB MICE

| Compound | Dose (mg/kg) | Reduction in Blood Glucose Level (%) | Triglyceride Lowering (%) |
| --- | --- | --- | --- |
| Example 14 | 3 mg | 60 | 46 |
| Example 22 | 3 mg | 64 | 47 |
| Example 23 | 3 mg | 63 | 41 |

The experimental results from the db/db mice, suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

Compounds can be tested in ob/ob mice and Zucker rats as described below.

The ob/ob mice at 5 weeks of age can be obtained from Bomholtgard, Denmark and can be used at 8 weeks of age. Zucker fa/fa fatty rats can be obtained from IffaCredo, France at 10 weeks of age and can be used at 13 weeks of age. The animals can be maintained under 12 hour light and dark cycle at 25±1° C. Animals can be given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes. 1988. 37: 1549–1558).

The test compounds can be administered at 0.1 to 30 mg/kg/day dose for 9 days. The control animals can receive the vehicle (0.25% carboxymethylcellulose, dose 10 ml/kg) through oral gavage.

The blood samples can be collected in fed state 1 hour after drug administration on 0 and 9 day of treatment. The blood can be collected from the retro-orbital sinus through heparinised capillary in EDTA containing tubes. After centrifugation, plasma samples can be separated for triglyceride, glucose, free fatty acid, total cholesterol and insulin estimations. Measurement of plasma triglyceride, glucose, total cholesterol can be done using commercial kits (Dr. Reddy's Laboratory, Diagnostic Division kits, Hyderabad, India). The plasma free fatty acid can be measured using a commercial kit from Boehringer Mannheim, Germany. The plasma insulin can be measured using a RIA kit (BARC, India). The reduction of various parameters examined is calculated according to the formula given below.

In ob/ob mice oral glucose tolerance test can be performed after 9 days treatment. Mice can be fasted for 5 hrs and challenged with 3 gm/kg of glucose orally and blood samples can be collected at 0, 15, 30, 60 and 120 min for estimation of plasma glucose levels.

b) Cholesterol Lowering Activity in Hypercholesterolemic Rat Models:

Male Sprague Dawley rats (NIN stock) were bred in DRF animal house. Animals were maintained under 12 hour light and dark cycle at 25±1° C. Rats of 180–200 gram body weight range were used for the experiment. Animals were made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74: 215–225).

The test compounds were administered orally at a dose 0.1 to 30 mg/kg/day for 3 days. Control group was treated with vehicle alone (0.25% Carboxymethylcellulose; dose 1 ml/kg).

The blood samples were collected in fed state 1 hour after drug administration on 0 and 3 day of compound treatment. The blood was collected from the retro-orbital sinus through heparinised capillary in EDTA containing tubes. After centrifugation, plasma sample was separated for total cholesterol, HDL and triglyceride estimations. Measurement of plasma triglyceride, total cholesterol and HDL were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

CHOLESTEROL LOWERING ACTIVITY IN MALE SPRAGUE RATS

| Compound | Dose mg/kg | Triglyceride (%)↓ | Total Cholesterol (%)↓ | HDL↑ (%) | LDL (%)↓ | VLDL(%)↓ |
| --- | --- | --- | --- | --- | --- | --- |
| Example 15 | 3 mg | 52 | 42 | 53 | 46 | 52 |

↓ = reduction; ↑ = increase; NE = no effect c) Plasma Triglyceride and Total Cholesterol Lowering Activity in Swiss Albino Mice and Guinea Pigs:

Male Swiss albino mice (SAM) were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20–25 g body weight range and Guinea pigs of 500–700 g body weight range were used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds were administered orally to Swiss albino mice at 0.3 to 30 mg/kg/day dose for 6 days. Control mice were treated with vehicle (0.25% Carboxymethylcellulose; dose 10 ml/kg). The test compounds were administered orally to Guinea pigs at 0.3 to 30 mg/kg/day dose for 6 days. Control animals were treated with vehicle (0.25% Carboxymethylcellulose; dose 5 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O., Ed., 1963. 211–214; Trinder, P. Ann. Clin. Biochem. 1969. 6: 24–27). Measurement of plasma triglyceride, total cholesterol and HDL were done using commercial kits (Dr. Reddy's Diagnostic Division, Hyderabad, India).

| TRIGLYCERIDE LOWERING ACTIVITY IN SWISS ALBINO MICE | | |
|---|---|---|
| Compound | Dose (mg/kg) | Triglyceride (%)↓ |
| Example 14 | 3 mg | 46 |
| Example 16 | 3 mg | 38 |
| Example 17 | 3 mg | 48 |
| Example 23 | 3 mg | 54 |
| Example 22 | 3 mg | 38 |

Formulae for Calculation:
1. Percent reduction in Blood sugar/triglycerides/total cholesterol were calculated according to the formula:

$$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels were calculated according to the formula:

LDL cholesterol in mg/dl =

$$\left[\text{Total cholesterol} - \text{HDL cholesterol} - \frac{\text{Triglyceride}}{5}\right] \text{mg/dl}$$

VLDL cholesterol in mg/dl =

$$[\text{Total cholesterol} - \text{HDL cholesterol} - \text{LDL cholesterol}] \text{mg/dl}.$$

What is claimed is:
1. A compound of formula (IVf)

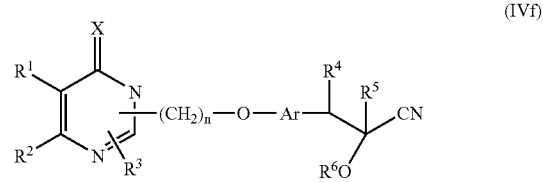

where X represents O or S;
the groups $R^1$, $R^2$ and the group $R^3$, when attached to the carbon atom, are the same or different, and represent hydrogen, halogen, hydroxyl, nitro, cyano, formyl or substituted or unsubstituted groups selected from alkyl, cycloalkyl, alkoxy, cycloalkoxy, aryl, aryloxy, aralkyl, aralkoxy, heterocyclyl selected from the group consisting of aziridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or an amide or ester of the carboxylic acid, or sulfonic acid or an amide or ester of the sulfonic acid; $R^3$ when attached to nitrogen atom represents hydrogen, hydroxyl, formyl or substituted or unsubstituted groups selected from alkyl, cyclo ($C_3$–$C_6$)alkyl, alkoxy, cycloalkoxy, aryl, aralkyl, aryloxy, aralkoxy, heterocyclyl selected from the group consisting of axiridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl groups, an amide or an ester of carboxylic acid or an amide or an ester of sulfonic acid;
the linking group represented by —$(CH_2)_n$—O— is attached either through nitrogen atom or through carbon atom where n is an integer ranging from 1–4;
Ar represents a substituted or unsubstituted, divalent, single or fused, aromatic or heterocyclic group selected from the group consisting of divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl and benzoxazolyl;
$R^4$ represents hydrogen atom, halogen, hydroxyl, lower alkyl, alkoxy or aralkyl group;
$R^5$ represents hydrogen or substituted or unsubstituted group selected from alkyl, cyclo ($C_3$–$C_7$)alkyl, aryl, aralkyl, heterocyclyl selected from the group consisting of aziridinyl, pyrrolidinyl and piperidinyl; heteroaryl selected from the group consisting of pyridyl, thienyl and furyl or heteroaralkyl groups; and R⁶ represents hydrogen or substituted or unsubstituted group selected from alkyl, acyl, cycloalkyl, aryl, aralkyl, heterocyclyl, heteroaryl, heteroaralkyl, alkoxyalkyl, alkoxycarbonyl, aryloxycarbonyl, and alkylaminocarbonyl, arylaminocarbonyl.

2. A compound of formula (IVg)

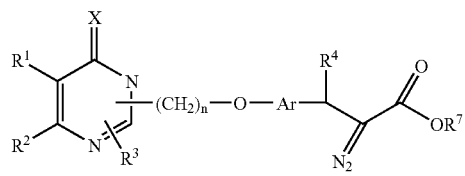

(IVg)

where X represents O or S;

the groups R¹, R² and the group R³, when attached to the carbon atom, are the same or different, and represent hydrogen, halogen, hydroxyl, nitro, cyano, formyl or substituted or unsubstituted groups selected from alkyl, cycloalkyl, alkoxy, cycloalkoxy, aryl, aryloxy, aralkyl, aralkoxy, heterocyclyl selected from the group consisting of aziridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or an amide or ester of the carboxylic acid, or sulfonic acid or an amide or ester of the sulfonic acid; R³ when attached to nitrogen atom represents hydrogen, hydroxyl, formyl or substituted or unsubstituted groups selected from alkyl, cyclo ($C_3$–$C_6$)alkyl, alkoxy, cycloalkoxy, aryl, aralkyl, aryloxy, aralkoxy, heterocyclyl selected from the group consisting of axiridinyl, pyrrolidinyl, morpholinyl, piperidinyl and piperazinyl; heteroaryl selected from the group consisting of pyridyl, thienyl, furyl, pyrrolyl, oxazolyl, thiazolyl, imidazolyl, oxadiazolyl, tetrazolyl, benzopyranyl and benzofuranyl; heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl groups, an amide or an ester of carboxylic acid or an amide or an ester of sulfonic acid;

the linking group represented by —$(CH_2)_n$—O— is attached either through nitrogen atom or through carbon atom where n is an integer ranging from 1–4;

Ar represents a substituted or unsubstituted, divalent, single or fused, aromatic or heterocyclic group selected from the group consisting of divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl and benzoxazolyl;

R⁴ represents hydrogen atom, halogen, hydroxyl, lower alkyl, alkoxy or aralkyl group;

R⁷ represents hydrogen or substituted or unsubstituted group selected from alkyl, acyl, cycloalkyl, aryl, aralkyl, heterocyclyl, heteroaryl, and heteroaralkyl.

* * * * *